US009554459B2

(12) United States Patent (10) Patent No.: US 9,554,459 B2
Gruenbacher et al. (45) Date of Patent: Jan. 24, 2017

(54) MICROFLUIDIC DELIVERY SYSTEM FOR RELEASING FLUID COMPOSITIONS

(71) Applicant: The Procter & Gamble Company, Cincinnati, OH (US)

(72) Inventors: Dana Paul Gruenbacher, Fairfield, OH (US); David S Hunt, San Diego, CA (US); Joseph Edward Scheffelin, Poway, CA (US); Simon Dodd, West Linn, OR (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/950,214

(22) Filed: Nov. 24, 2015

(65) Prior Publication Data

US 2016/0081181 A1 Mar. 17, 2016

Related U.S. Application Data

(63) Continuation of application No. 14/310,285, filed on Jun. 20, 2014, now Pat. No. 9,211,980.

(51) Int. Cl.
*B41J 2/175* (2006.01)
*B41J 2/14* (2006.01)
(Continued)

(52) U.S. Cl.
CPC ............ *H05K 1/0272* (2013.01); *A61L 9/14* (2013.01); *B41J 2/1404* (2013.01); *B41J 2/1433* (2013.01);
(Continued)

(58) Field of Classification Search
CPC ..... B41J 2/1404; B41J 2/14072; B41J 2/1408; B41J 2/14153; B41J 2/1433; B41J 2/17513; B41J 2/17523; B41J 2/17546; B41J 2/17553; B41J 2/17506; B65D 43/02; B65D 83/00; H05K 1/0272; H05K 1/11; A45D 34/00; A45D 2034/005; F16F 1/18; G03G 15/0435
See application file for complete search history.

(56) References Cited

U.S. PATENT DOCUMENTS 5,084,713 A * 1/1992 Wong ..................... B41J 2/1408
347/18
5,317,339 A * 5/1994 Braun .................. B41J 2/17513
29/890.1
(Continued)

FOREIGN PATENT DOCUMENTS

CN 1223637 C 10/2005
CN 101 020 073 A 8/2007
(Continued)

OTHER PUBLICATIONS

PCT Search Report dated Jun. 19, 2015; PCT/US2015/036546, 5 Pages.
(Continued)

*Primary Examiner* — Anh T. N. Vo
(74) *Attorney, Agent, or Firm* — Abbey A. Lopez

(57) ABSTRACT

A microfluidic refill includes a reservoir having a hollow body and an opening; a transport member in fluid communication with the reservoir; and a lid enclosing the opening of the reservoir. The lid is in fluid communication with the transport member. The lid comprises a rigid microfluidic delivery member. The rigid microfluidic delivery member includes a die and electrical traces that are in electrical communication with the die, wherein the electrical traces terminate at electrical contacts, wherein the electrical traces are disposed on only one plane. The die has a fluid chamber in fluid communication with the transport member at an inlet of the fluid chamber and with an orifice at an outlet of the fluid chamber and.

8 Claims, 30 Drawing Sheets

(51) Int. Cl.
  *H05K 1/11* (2006.01)
  *H05K 1/02* (2006.01)
  *B65D 43/02* (2006.01)
  *B65D 83/00* (2006.01)
  *A61L 9/14* (2006.01)

(52) U.S. Cl.
  CPC ............ *B41J 2/14072* (2013.01); *B65D 43/02* (2013.01); *B65D 83/00* (2013.01); *H05K 1/11* (2013.01); *Y10T 29/49732* (2015.01)

(56) References Cited

U.S. PATENT DOCUMENTS

| | | | |
|---|---|---|---|
| 5,610,635 A * | 3/1997 | Murray | B41J 2/1752 347/19 |
| 5,975,675 A | 11/1999 | Kim | |
| 6,010,210 A | 1/2000 | Wilson et al. | |
| 6,113,228 A * | 9/2000 | Pawlowski, Jr. | B41J 2/17503 347/81 |
| 6,170,937 B1 | 1/2001 | Childers et al. | |
| 6,261,347 B1 | 7/2001 | Moreland | |
| 6,325,475 B1 | 12/2001 | Hayes et al. | |
| 6,371,451 B1 * | 4/2002 | Choi | A45D 34/02 261/115 |
| 6,834,937 B2 * | 12/2004 | Killmeier | B41J 2/1753 347/50 |
| 7,201,916 B2 * | 4/2007 | Schiavo | A01M 1/2077 424/40 |
| 7,367,661 B2 | 5/2008 | Hess et al. | |
| 8,020,573 B2 | 9/2011 | Lamers et al. | |
| 8,251,500 B2 | 8/2012 | Yamada et al. | |
| 2002/0192255 A1 | 12/2002 | Schiavo et al. | |
| 2004/0032468 A1 | 2/2004 | Killmeier et al. | |
| 2006/0065755 A1 | 3/2006 | Sugita et al. | |
| 2010/0154790 A1 | 6/2010 | Merassi et al. | |
| 2014/0078229 A1 | 3/2014 | Jackson et al. | |

FOREIGN PATENT DOCUMENTS

| | | |
|---|---|---|
| GB | 2410468 A | 3/2005 |
| JP | 2005185366 A | 7/2005 |
| JP | 2005224504 A | 8/2005 |
| JP | 2007054446 A | 3/2007 |
| KR | 100238582 B1 | 1/2000 |
| WO | WO 2004/044552 A2 | 5/2004 |
| WO | WO 2014/043424 A1 | 3/2014 |

OTHER PUBLICATIONS

PCT Search Report dated Sep. 17, 2015; PCT/US2015/036549, 11 Pages.
PCT Search Report dated Sep. 18, 2015; PCT/US2015/036551, 9 Pages.
U.S. Appl. No. 14/310,401, filed Jun. 20, 2014, Dana Paul Gruenbacher, et al.
U.S. Appl. No. 14/310,285, filed Jun. 20, 2014, Dana Paul Gruenbacher, et al.
U.S. Appl. No. 14/310,311, filed Jun. 20, 2014, Dana Paul Gruenbacher, et al.
U.S. Appl. No. 14/310,334, filed Jun. 20, 2014, Dana Paul Gruenbacher, et al.
U.S. Appl. No. 14/310,367, filed Jun. 20, 2014, Dana Paul Gruenbacher, et al.

* cited by examiner

MICROFLUIDIC DELIVERY SYSTEM FOR RELEASING FLUID COMPOSITIONS

FIELD

The present disclosure generally relates to a system for delivering a fluid composition into the air, and, more particularly, relates to a microfluidic delivery system, including a microfluidic delivery refill for delivering fluid compositions through thermal activation of the fluid composition, such as perfume compositions, into the air, for example.

BACKGROUND

Various systems exist to deliver volatile compositions, such as perfume compositions, into the air by an energized (i.e. electrically/battery powered) microfluidic atomization. Recent attempts have been made to deliver scents using thermally activated microfluidic delivery systems, and, particularly, thermal inkjet systems. Some of these attempts are directed to printing ink-based scented fluids onto a substrate or surface medium using methods similar to those for printing ink onto a substrate or surface.

Thermal inkjet technology utilizes a replaceable cartridge that contains fluid and a micro-electro-mechanical system ("MEMS") based print head that controls the release of the fluid from the cartridge. Some cartridges for printing fluid onto a substrate include a flexible circuit to provide electrical communication between the cartridge and the dispensing device. In order to locate the substrate to be printed in close proximity with the inkjet cartridge, the electrical connections on the inkjet cartridge must be positioned away from the substrate. As a result, the electrical connections on the flexible circuit may be disposed on a different plane as an orifice where the ink is released from the inkjet cartridge. Thus, when inserting a new inkjet cartridge into the printer, the inkjet cartridge needs to be connected with the printer relative to at least two planes. This may cause limitations in the design of the printer and the access to the inkjet cartridge, as well as increase the complexity of replacing the inkjet cartridge. Moreover, some flexible circuit structures are relatively complicated to manufacture and to attach to a cartridge of a complex shape.

Further, the flexible circuit structures may be made of expensive materials such as polyimide. In addition, the flexibility of the circuit board may have poor electrical connection between the inkjet cartridge and the printer. This is due to the fact that the connection points of the flexible circuit structure may oxidize over time, especially in the presence of certain chemical vapors, causing the electrical connection between the inkjet cartridge and the printer to be diminished.

As a result, it would be beneficial to provide a microfluidic delivery system for delivering a fluid composition into the air that uses relatively inexpensive circuit boards that are also easy to manufacture. Moreover, it would be beneficial to provide a microfluidic delivery system that provides for strong and reliable electrical connection between the refill and the microfluidic delivery system. In addition, it would be beneficial to provide a microfluidic delivery system and refill that are relatively simple to replace.

SUMMARY

Aspects of the present disclosure include a microfluidic delivery refill comprising a reservoir having a hollow body and an opening; a transport member in fluid communication with the reservoir; and a lid enclosing the opening of the reservoir. The lid is in fluid communication with the transport member. The lid comprises a rigid microfluidic delivery member. The microfluidic delivery member comprises a die and electrical traces that are in electrical communication with the die. The electrical traces terminate at electrical contacts. The electrical traces are disposed on only one plane. The die comprises a fluid chamber in fluid communication with the transport member at an inlet of the fluid chamber and an orifice at an outlet of the fluid chamber.

Aspects of the present disclosure include a thermally activated microfluidic delivery system comprising a housing and a refill releasably connectable with the housing. The refill comprises a reservoir having a hollow body and an opening and a lid enclosing the opening of the reservoir. The lid comprises a rigid microfluidic delivery member. The microfluidic delivery member comprises a die and electrical traces that are in electrical communication with the die. The electrical traces terminate at electrical contacts. The electrical traces are disposed on only one plane. The housing defines an interior and an exterior of the microfluidic delivery system. The housing comprises a holder member disposed in the interior space of the housing. The fluid delivery refill is slideably connects with the holder member.

Aspects of the present disclosure include a method of refilling a thermally activated microfluidic delivery system with a refill, wherein the refill comprises reservoir having a hollow body and an opening, a lid enclosing the opening of the reservoir. The lid comprises a microfluidic delivery member having a die and electrical traces that are in electrical communication with the die. The electrical traces terminate at electrical contacts. The electrical traces are disposed on only one plane. The method comprising the steps of: providing a housing that defines an interior and an exterior, wherein the housing comprises a holder member disposed in the interior of the housing; and sliding the fluid delivery refill into the holder member in a direction parallel with the plane the electrical traces are disposed on.

DETAILED DESCRIPTION

Figure 1:
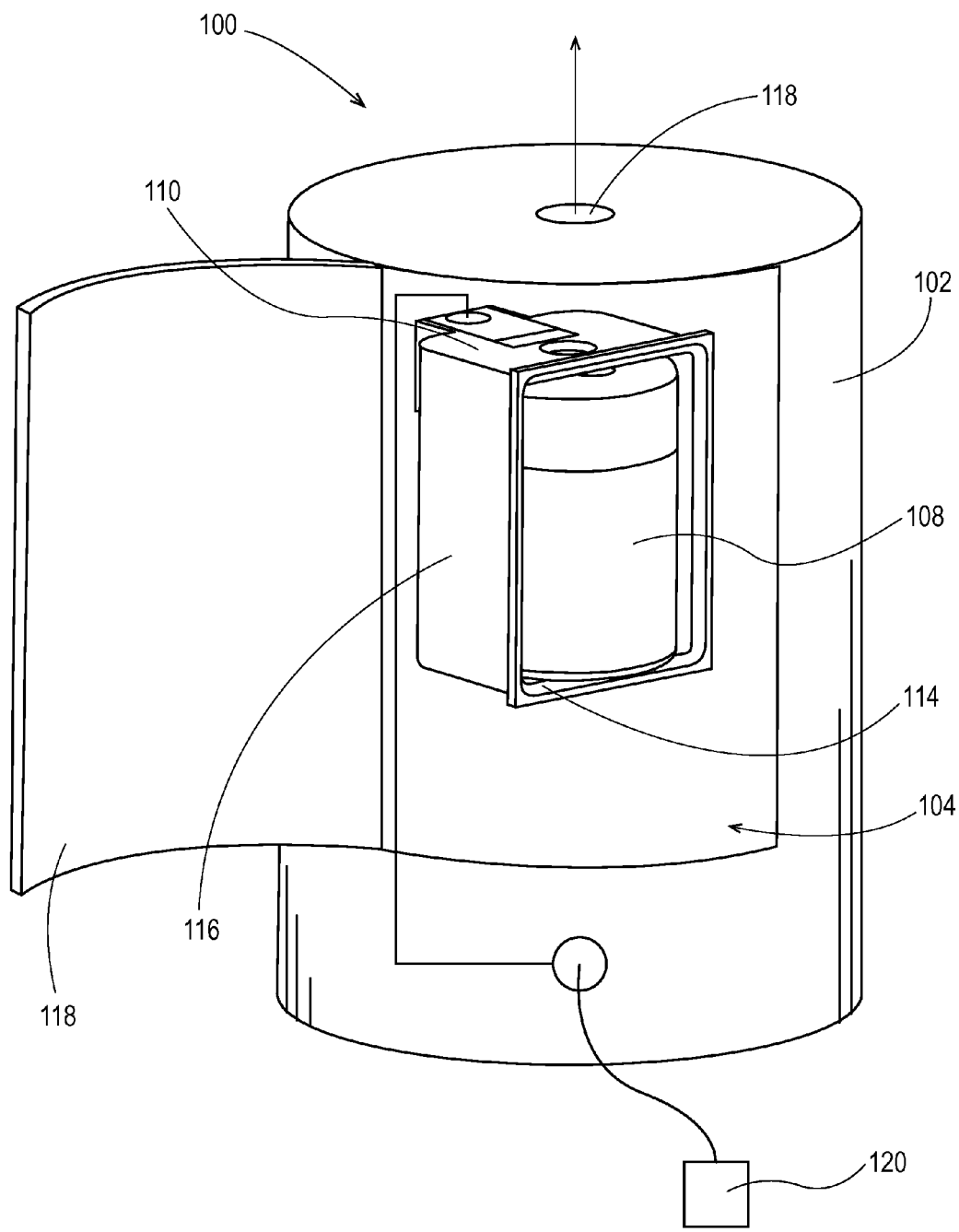
FIG. 1 is a schematic, perspective view of a microfluidic delivery system.

Various non-limiting configurations of the present disclosure will now be described to provide an overall understanding of the principles of the structure, function, manufacture, and use of the microfluidic delivery systems for delivering fluid compositions into the air disclosed herein. One or more examples of these non-limiting configurations are illustrated in the accompanying drawings. Those of ordinary skill in the art will understand that the microfluidic delivery systems described herein and illustrated in the accompanying drawings are non-limiting example configurations and that the scope of the various non-limiting embodiments of the present disclosure are defined solely by the claims. The features illustrated or described in connection with one non-limiting configuration may be combined with the features of other non-limiting configurations. Such modifications and variations are intended to be included within the scope of the present disclosure.

The present disclosure includes a microfluidic delivery system for delivering a fluid composition into the air. For example, the microfluidic delivery system may be used to deliver a perfume composition into the air. The microfluidic delivery system comprises a housing defining an interior and an exterior of the microfluidic delivery system and a holder member disposed in the interior of the microfluidic delivery system. The microfluidic delivery system includes a refill that is releasably connectable with the holder member of the housing. The microfluidic delivery system also includes a power source. The refill is configured to thermally activate a fluid composition to release the fluid composition into the air.

The refill of the present disclosure includes a reservoir for holding a fluid composition, a transport member that is in fluid communication with the reservoir, and a lid that encloses the opening of the reservoir. The lid comprises a rigid microfluidic delivery member for delivering the fluid composition into the air. The microfluidic delivery member includes a microfluidic die. The term "microfluidic die", as used herein means a die comprising a fluid injection system made using a semiconductor micro fabrication process such as thin film deposition, passivation, etching, spinning, sputtering, masking, epitaxy growth, wafer/wafer bonding, micro thin-film lamination, curing, dicing, etc. These processes are known in the art to make MEMs devices. Microfluidic dies may be made from silicon, glass, or a mixture thereof. The microfluidic die comprises a plurality of microfluidic chambers, each comprising a corresponding actuation element: a heating element or an electromechanical actuator. In this way, the microfluidic die's fluid injection system may be micro thermal nucleation (e.g. via heating element) or micro mechanical actuation (e.g. via thin film piezoelectric or ultrasonics). One type of microfluidic die suitable for the microfluidic delivery system of the present invention is an integrated membrane of nozzles obtained via MEMs technology as described in U.S. 2010/0154790, assigned to STMicroelectronics S.R.I., Geneva, Switzerland. In the case of thin film piezo, the piezoelectric material is typically applied via spinning and/or sputtering processes. The semiconductor micro fabrication process allows one to simultaneously make one or thousands of MEMS devices in one batch process (a batch process comprises of multiple mask layers). The microfluidic delivery member includes a die having a fluid chamber with an inlet and an outlet. The inlet of the fluid chamber is in fluid communication with the transport member and the outlet of the fluid chamber is in fluid communication with an orifice. The microfluidic delivery member also comprises electrical leads that terminate at electrical contacts to provide electrical communication from the power source of the microfluidic delivery system to the die of the microfluidic delivery member. The electrical leads are disposed on only one plane. The electrical contacts and the die may be disposed on substantially parallel planes, and, in some exemplary configurations, the electrical contacts and the die may be disposed on the same plane. The orifice of the die may open in a direction that is perpendicular to the plane the electrical leads are disposed upon.

The refill may be slideably connectable with the housing. The refill may be inserted into the microfluidic delivery system by sliding the refill into the holder member in a direction parallel with the plane the electrical traces are disposed on. A wall of the holder member may comprise electrical contacts that are configured to connect with the electrical contacts of the refill. The electrical contacts of the refill may have a top surface that connects to the electrical contacts of the holder member.

In operation, the fluid composition travels from the reservoir, into the transport member, and into the die. In the die, the fluid composition travels into the fluid chamber and is heated in order to volatilize a portion of the fluid composition, producing a vapor bubble that causes a droplet of fluid composition to be released through the orifice of the die. The droplet of fluid composition is released from the refill and exits through the aperture of the housing into the air.

Once the fluid composition is depleted from the refill, the refill may be removed from the housing and a new refill may be connected with the housing of the microfluidic delivery system. In other exemplary configurations, the refill may be refilled with additional fluid composition once the fluid composition is depleted.

The microfluidic delivery member may be configured as a separate component that is attached with the lid, or may be integrally formed with the lid. In an exemplary configuration wherein the microfluidic delivery member is a separate element, the microfluidic delivery member may be configured in the form of a circuit board that includes the die and the electrical contacts. The circuit board may be comprised of a rigid material to provide a robust mechanical interface between electrical contacts on the circuit board and electrical contacts on the holder member. In such an exemplary configuration, the circuit board may be connected with the exterior of the lid. In other exemplary configurations, the microfluidic delivery member may be integrally formed with the lid. In such an exemplary configuration, the lid may be composed of a rigid material to provide a strong electrical connection with the electrical contacts on the holder member.

While the present disclosure discusses the use of a microfluidic delivery system for delivering perfume compositions into the air, it is to be appreciated that the microfluidic delivery system of the present disclosure may be used to delivery various other fluid compositions into the air. For example, the microfluidic delivery system may be used to deliver cosmetic compositions, lotion compositions, cleaning compositions, and various other compositions for use in any industry.

Figure 2:
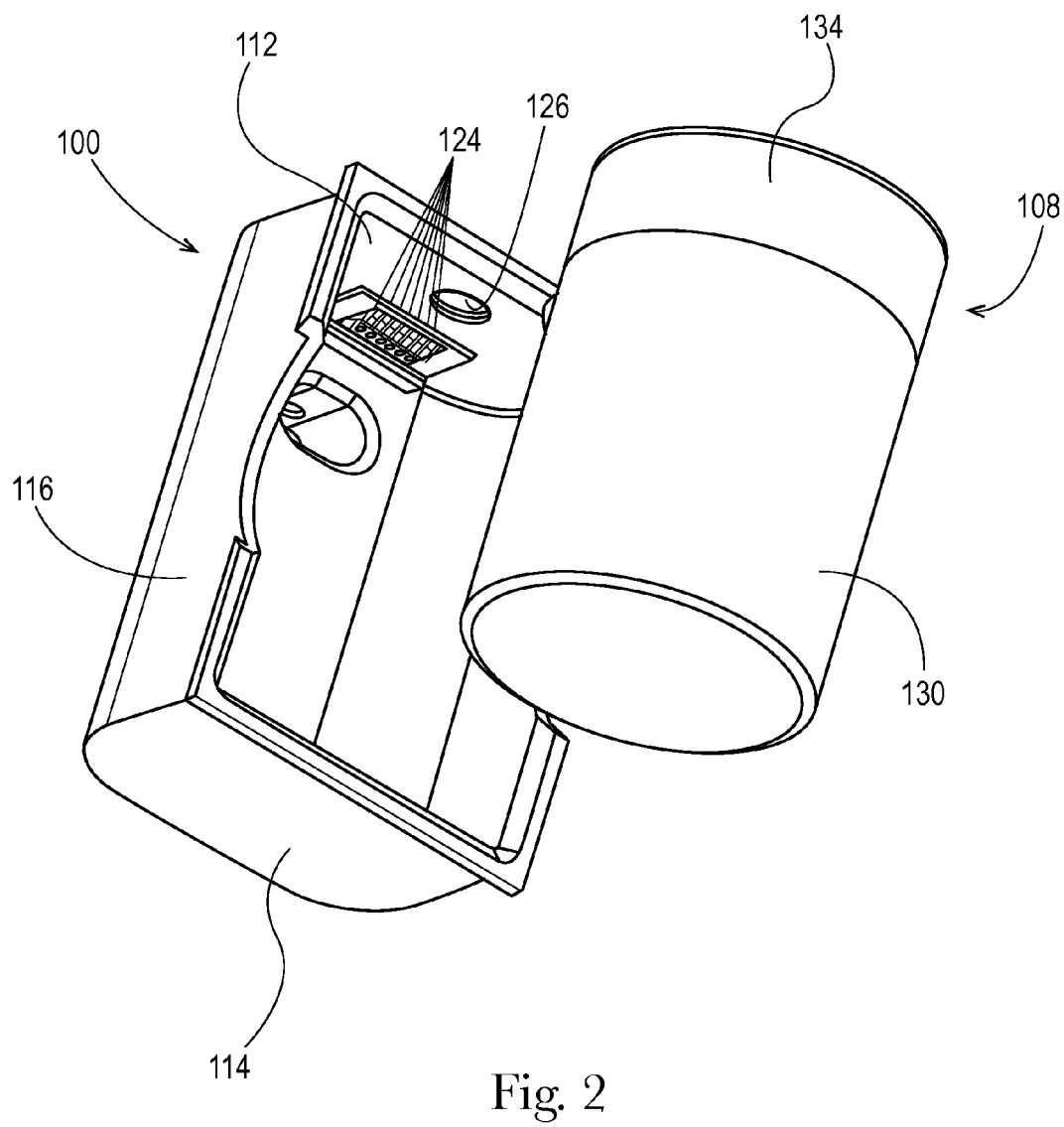
FIG. 2 is a perspective view of a holder member and a refill of a microfluidic delivery system.

As shown in FIGS. 1 and 2, a microfluidic delivery system 100 comprises a housing 102 defining an interior 104 and an exterior 106 of the microfluidic delivery system 100. The housing 102 may include a holder member 110 disposed in the interior 104 of the microfluidic delivery system 100. The housing 102 may comprise a door 118 for accessing the interior 104 of the microfluidic delivery system 100. The holder member 110 includes an aperture 126. The holder member 110 also includes electrical contacts 124.

The microfluidic delivery system 100 also includes a refill 108 that is releasably connectable with the holder member 110. The refill 108 may use thermal heating to release a fluid composition contained within the refill 108 into the air. The refill 108 may be releasably connectable with the housing 102. The housing 102 includes an aperture 118 for delivering a fluid composition from the refill 108 into the air at the exterior 106 of the microfluidic delivery system 100. The aperture 126 of the holder member 110 and the aperture 118 of the housing 102 are aligned. The microfluidic delivery system 100 also includes a power source 120 that is in electrical communication with the electrical contacts 124 of the holder member 110.

In some exemplary configurations, as shown in FIG. 2, the refill 108 is slideably connectable with the holder member 110. The refill 108 may be releasably connected or slideably connected with the holder member 110 in various ways. For example, the refill 108 may be connected with the holder member 110 using a lock and key system to minimize the likelihood that an improper refill is used in the microfluidic delivery system 100.

Figure 3:
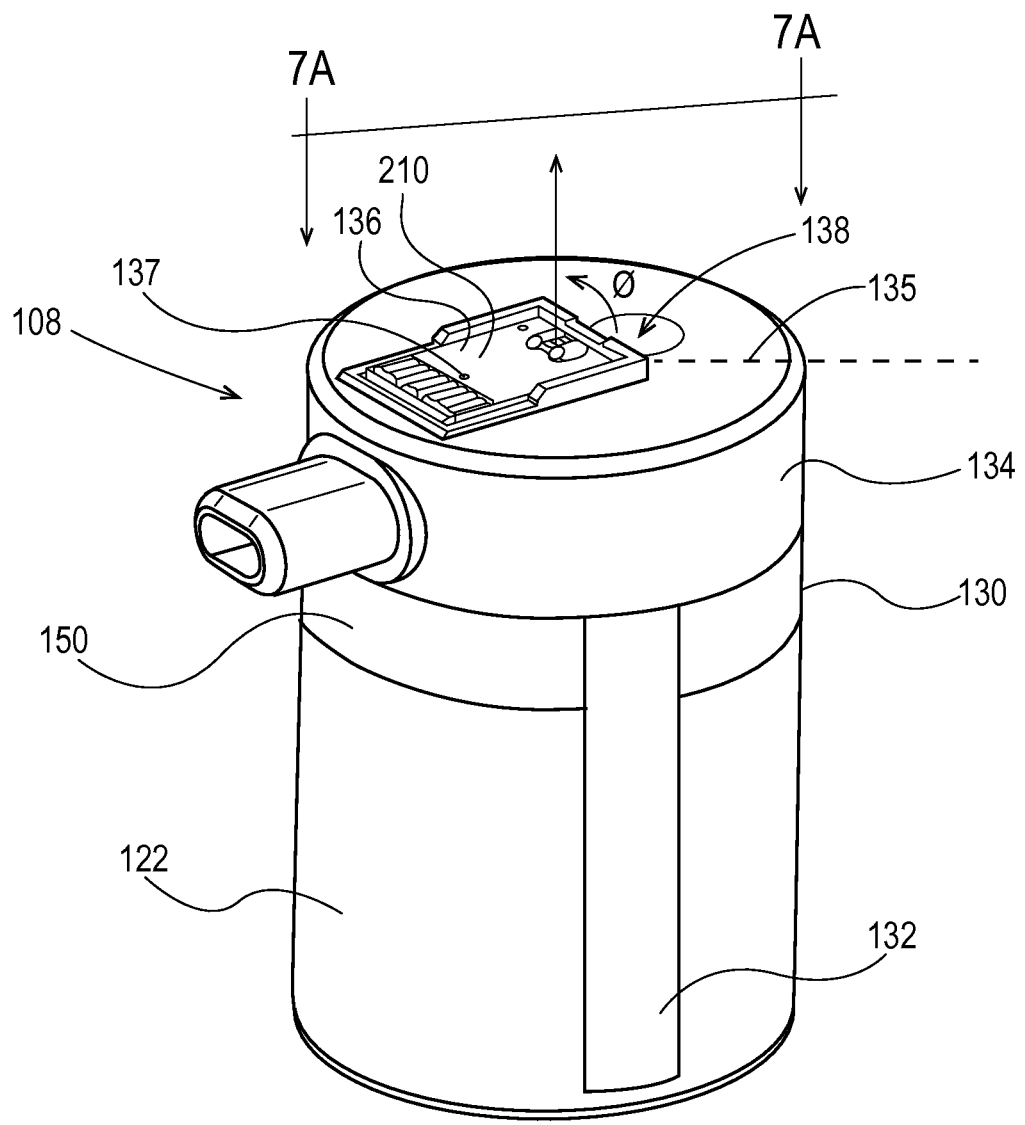
FIG. 3 is a perspective view of a refill.

As shown in FIG. 3, the refill 108 includes a reservoir 130 for holding a fluid composition 122, a transport member 132 that is in fluid communication with the reservoir 130, and a lid 134 that encloses the reservoir 130. The lid 134 comprises a rigid microfluidic delivery member 136 for delivering the fluid composition 122 contained within the reservoir 130 into the air.

Figure 4:
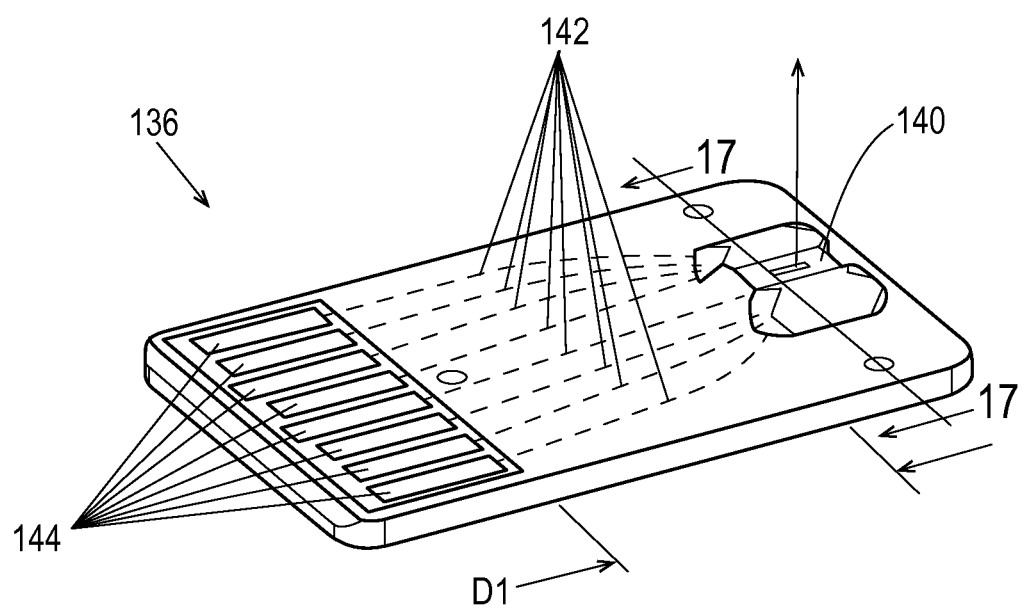
FIG. 4 is a perspective view of a microfluidic delivery member.

With reference to FIGS. 3 and 4, the microfluidic delivery member 136 includes a die 140 and electrical leads 142 that provide electrical communication from the power source of the microfluidic delivery system to the die 140 of the microfluidic delivery member 136. The electrical leads 142 of the microfluidic delivery member 136 comprise electrical contacts 144 disposed at an end portion of the electrical leads 142 most distant from the die 140. With reference to FIGS. 2 and 4, the electrical contacts 144 of the microfluidic delivery member 136 are in electrical communication with the electrical contacts 124 of the holder member 124.

Figure 5:
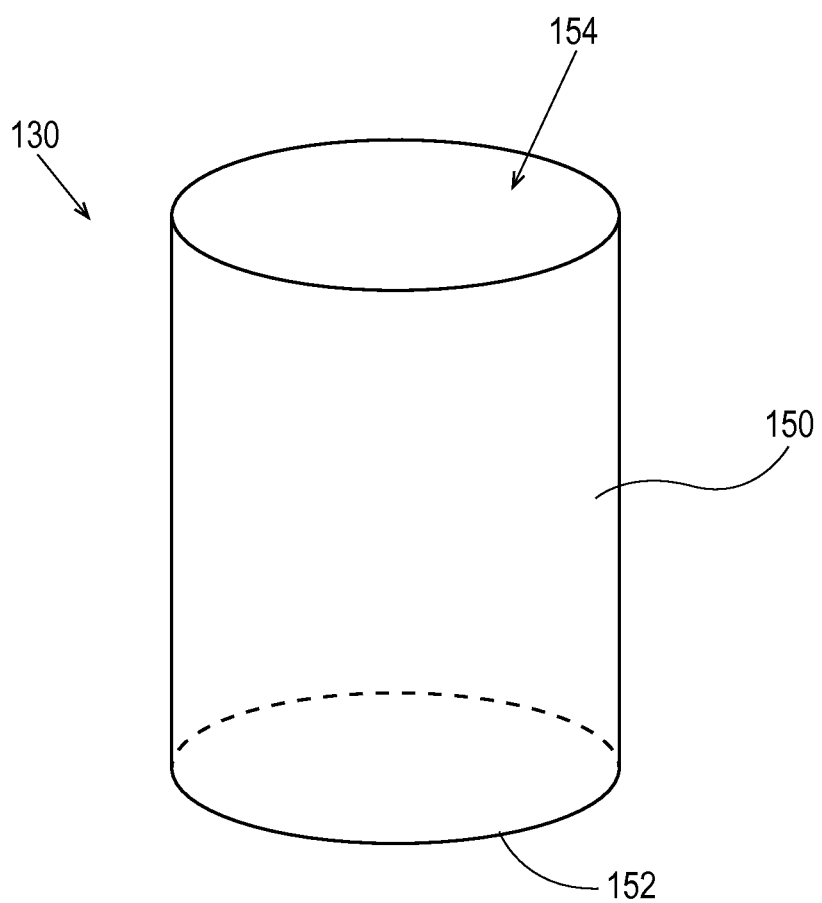
FIG. 5 is a perspective view of a cylindrical-shaped reservoir of a refill.
Figure 6:
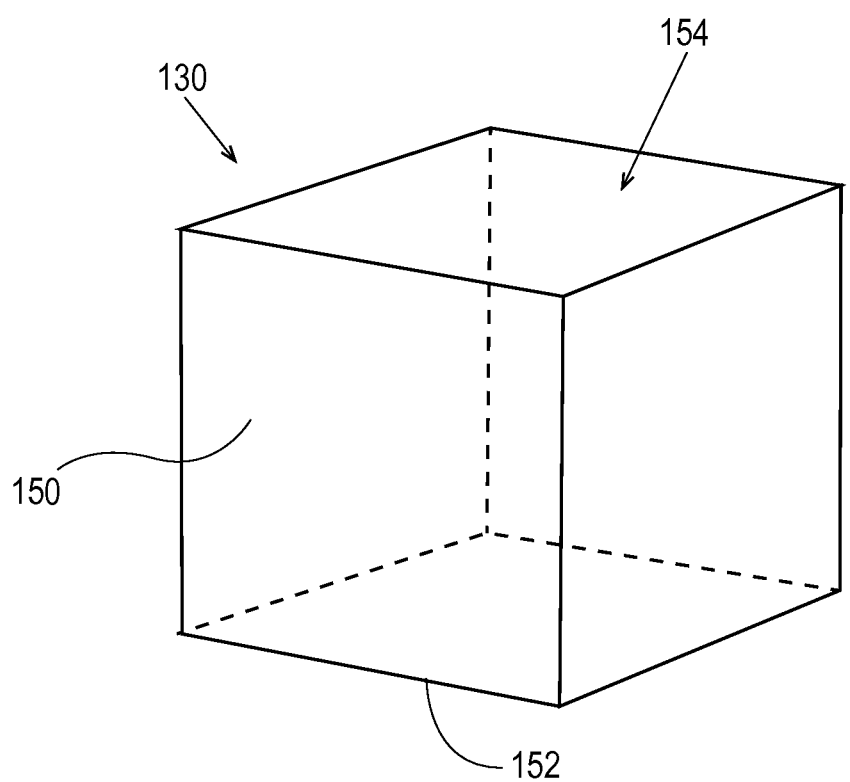
FIG. 6 is a perspective view of a cube-shaped reservoir of a refill.

With reference to FIG. 5, the reservoir 130 is configured as a hollow body for containing a fluid composition therein. The reservoir 130 may include one or more adjoining walls 150, a base 152 connected with the walls 150, and an opening 154 opposite the base 152. The reservoir 130 may be configured in various different shapes. For example, the reservoir 130 may have a cylindrical shape as shown in FIG. 5, or may have a cube-like shape as shown in FIG. 6. The reservoir 130 may comprise various materials, including glass or rigid polymeric materials such as polyester or polypropylene. The reservoir 130 may be configured to have various different dimensions. For example, the reservoir 130 may have a height $H_R$ of from about 20 mm to about 60 mm, and the base 152 may have a width $W_R$ of from about 15 mm to about 40 mm. The reservoir may be transparent, translucent, or opaque. In some exemplary configurations, a single microfluidic delivery system may be configured to receive refills 108 having various different size reservoirs 130 for containing different amounts of fluid composition.

Figure 7A:
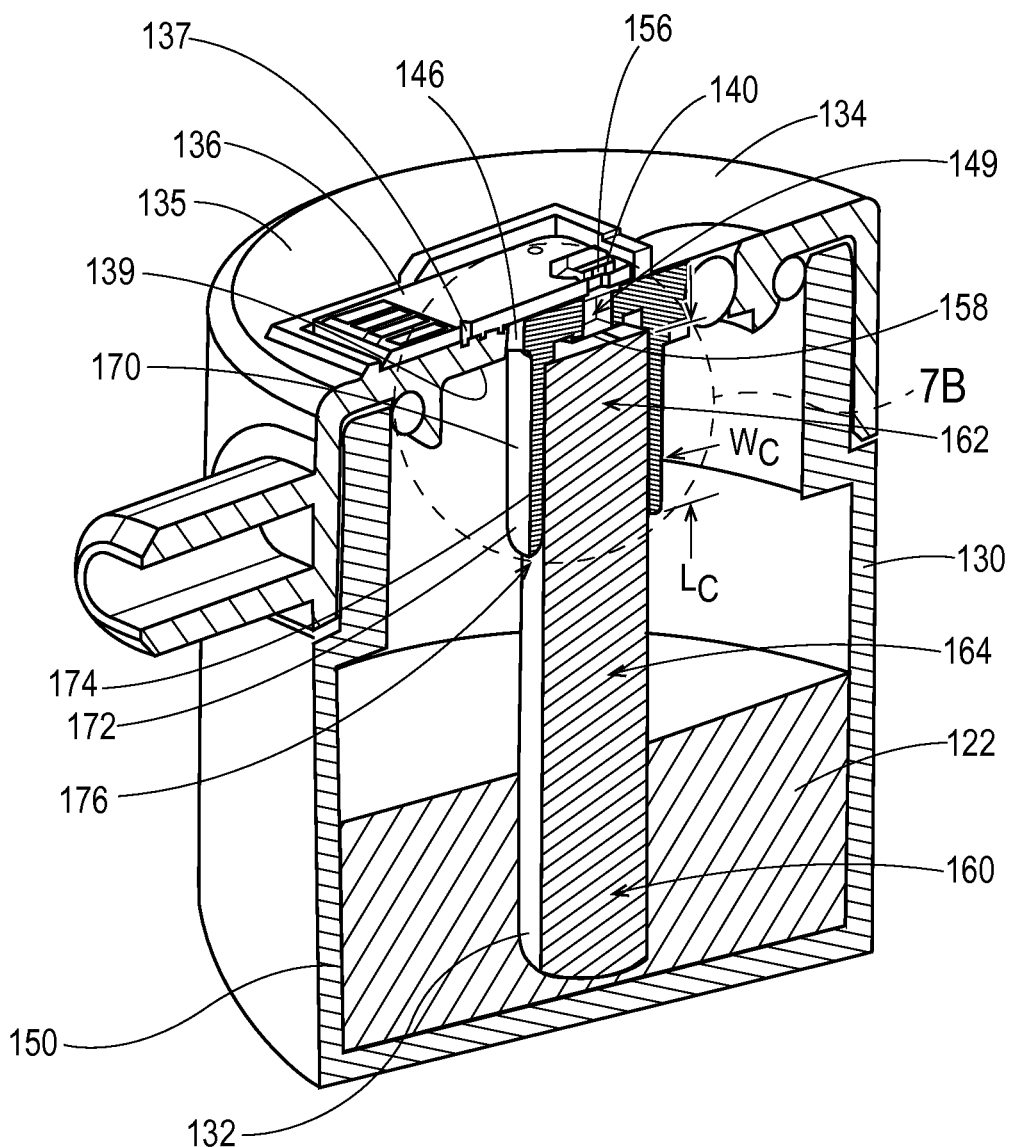
FIG. 7A is a sectional view of the refill of FIG. 3 taken along line 7A-7A.

With reference to FIGS. 3 and 7A, in some exemplary configurations, the transport member 132 is a porous structure that provides capillary forces to draw the fluid composition 122 from the reservoir 130 and to the microfluidic delivery member 136. The transport member 132 may define a first end portion 160, a second end portion 162, and a central portion 164 separating the first and second end portions 160 and 162. The first end portion 160 of the transport member 132 is in fluid communication with the fluid composition 122 and the second end portion 162 is in fluid communication with the die 140. The second end portion 162 of the transport member 132 may extend at least partially outside the reservoir 130. The first end portion 160 may be in fluid communication with the base 152 of the reservoir 130 in order to deliver fluid composition to the die 140 even when the level of fluid composition in the reservoir 130 is low. In some exemplary configurations, the transport member 132 may be completely surrounded by the walls 150 of the reservoir 130. Depending upon the configuration of the microfluidic delivery system 100, the fluid composition 122 may travel up or down the transport member 132. In some exemplary configurations, the fluid composition 122 travels up the transport member, in opposition to gravity.

In other exemplary configurations, the transport member 132 may be configured to deliver fluid composition to the die in other ways. For example, the transport member 132 may comprise a mechanical pump to transport the fluid composition from the reservoir 130 to the die 140. In other exemplary configurations, the transport member 132 may comprise a sponge. The transport member 132 may be configured with a spring to provide pressure to the sponge to feed the fluid composition to the die 140. In other exemplary configurations, the refill 108 may be pressurized, using aerosol or a bag-in-bottle technology for example, to feed the fluid composition to the die 140.

Figure 8:
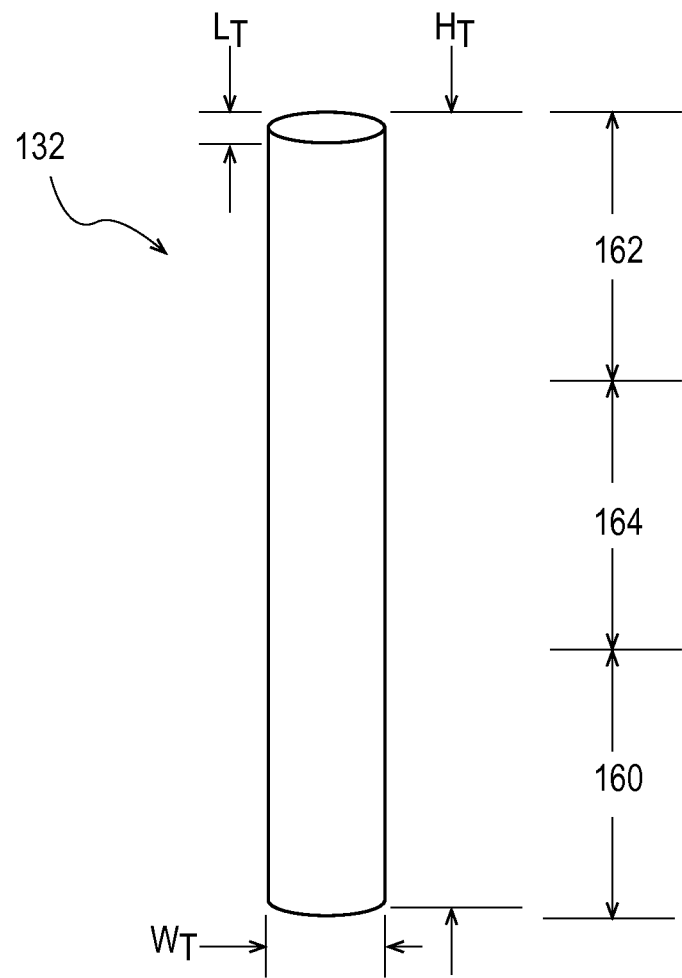
FIG. 8 is a front, elevation view of a transport member of a refill.

The transport member 132 may be configured to have various different shapes. For example, the transport member 132 may have a cylindrical as shown in FIG. 8, or an elongate cube shape. The transport member 132 may be defined by a height $H_T$, a length $L_T$, and a width $W_T$. The transport member 132 may have various heights. For example, the height $H_T$ of the transport member 132 may be in the range of about 1 mm to about 100 mm, or from about 5 mm to about 75 mm, or from about 10 mm to about 50 mm. The transport member 132 may have various lengths. For example, the length $L_T$ of the transport member 132 may be in the range of about 15 mm to about 55 mm. The transport member 132 may have various widths. For example, the width $W_T$ of the transport member 132 may be in the range of about 3 mm to about 10 mm.

The transport member 132 may be composed of various materials, such as polymer fibers or particles. Exemplary polymers used for the transport member include polyethylene, ultra-high molecular weight polyethelene (UHMW), nylon 6 (N6), polypropylene (PP), polyester fibers, ethyl vinyl acetate, polyether sulfone, polyvinylidene fluoride (PVDF), and polyethersulfone (PES), polytetrafluroethylene (PTFE), and combinations thereof. The transport member 132 may alternatively be composed of other materials such as fibrous or particulate metals, and fibrous carbon.

In some exemplary configurations, the transport member 132 is free of a polyurethane foam. Many ink jet refill cartridges use an open cell polyurethane foam which can be incompatible with some fluid compositions, such as perfume compositions, over time (e.g. after 2 or 3 months) and can break down.

In exemplary configurations where capillary transport is used to deliver fluid composition to the die 140, the transport member may exhibit an effective pore size. The transport member 132 may exhibit an average effective pore size from about 10 microns to about 500 microns, alternatively from about 50 microns to about 150 microns, alternatively about 70 microns. The average pore volume of the transport member 132 is from about 15% to about 85%, alternatively from about 25% to about 50%, or about 38%.

In some exemplary configurations, such as when the fluid composition comprises a perfume composition, the transport member may be configured with a high density composition to aid in containing the scent of the perfume composition. In one embodiment, the transport member is made from a plastic material chosen from high-density polyethylene (HDPE). As used herein, a high density transport member may include various materials having a pore diameter or equivalent pore diameter (e.g. in the case of fiber based wicks) ranging from about 20 microns to about 150 microns, alternatively from about 30 microns to about 70 microns, alternatively from about 30 microns to about 50 microns, alternatively, about 40 microns to about 50 microns.

As shown in FIGS. 3 and 7A, the lid 134 is connected with, and provides an enclosure to, the reservoir 130. The lid 134 may be configured in various ways. The lid 134 may be rigid. The lid 134 may be composed of various materials, including a solid polymeric material such as polyester or polypropylene. The lid 134 may connect with the reservoir 130 in various ways. For example, the lid 134 may be threaded onto the reservoir 130 or may snap onto the reservoir 130 using various types of fasteners. In some exemplary configurations, the lid 134 and the reservoir 130 may be integrally formed. In some exemplary configurations, the lid 134 may be releasably connectable with the reservoir 130. While, in other exemplary configurations, the lid 134 may be permanently or semi-permanently connected with the reservoir 130.

Figure 9:
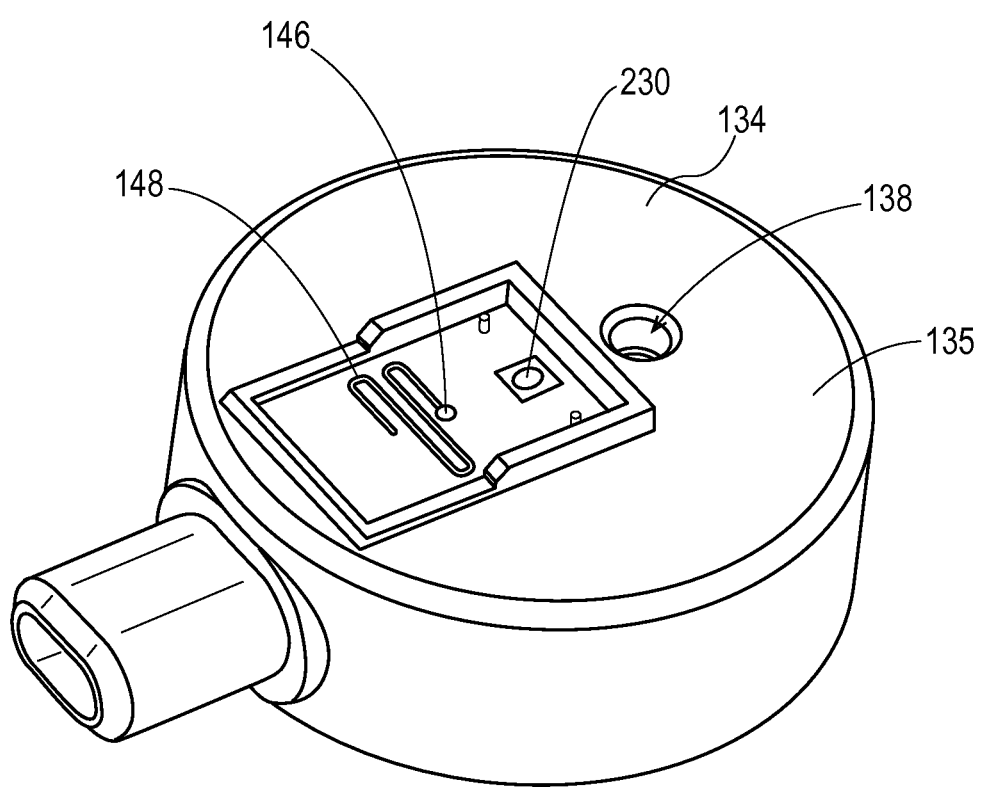
FIG. 9 is a perspective view of a lid of a refill.

As shown in FIGS. 7A and 9, the lid 134 may comprise a fill port 138 to fill the reservoir 130 with fluid composition. As such, the refill 108 may be filled with fluid composition either with the lid 134 connected with the reservoir 130, or with the lid 134 removed from the reservoir 130.

In some exemplary configurations, the lid 134 may comprise a vent port 146 so that air is able to replace the fluid composition which is released from the refill 108. The vent port 146 may be in fluid communication with a vent channel 148 in the lid 134 that directs the air into the reservoir 130 through a vent port 137 in the microfluidic delivery member 136.

As shown in FIG. 7A, the lid 134 may comprise an adapter 170 that connects the transport member 132 with the lid 134. The adapter 170 may be integrally formed with the lid 134, or the adapter may be a separate component that is connected with an inner surface 139 of the lid 134. The adapter 170 may be composed of the same material as the lid 134, or may be composed of a different material. The adapter 170 may be composed of various materials. For example, the adapter 170 may be composed of a rigid polymer such as polyester or polypropylene. An exemplary adapter is described in U.S. patent application Ser. No. 14/310,311 titled "MICROFLUIDIC DELIVERY SYSTEM", filed on Jun. 18, 2014.

As shown in FIG. 7A, the lid 134 includes an aperture 149 to provide fluid communication between the transport member 132 and the die 140.

As shown in FIG. 7A, the refill 108 may also comprise a filter 158 to prevent particles from entering the die 140 and clogging the fluid passages. The filter 158 may be positioned between the transport member 132 and lid 134. The filter 158 may be configured as a porous structure having interstitial spaces that allow the fluid composition to pass easily, but block particles of a certain size from entering the die 140. For example, the filter 158 may block particles that have a dimension greater than about one-third the size of the smallest fluid passage in the die 140. In some exemplary configurations, the filter 158 is connected with the lid 134 such that the fluid composition passes from the transport member 132, through the filter 158, through the aperture 149 in the lid 134, and to the die 140. The filter 158 may be attached with the lid 134 using an adhesive, such as an epoxy adhesive, for example. It is to be appreciated that the transport member 132 may also act as a filter, depending upon the size of the particles passing through the transport member 132 and the configuration of the transport member 132.

Figure 10:
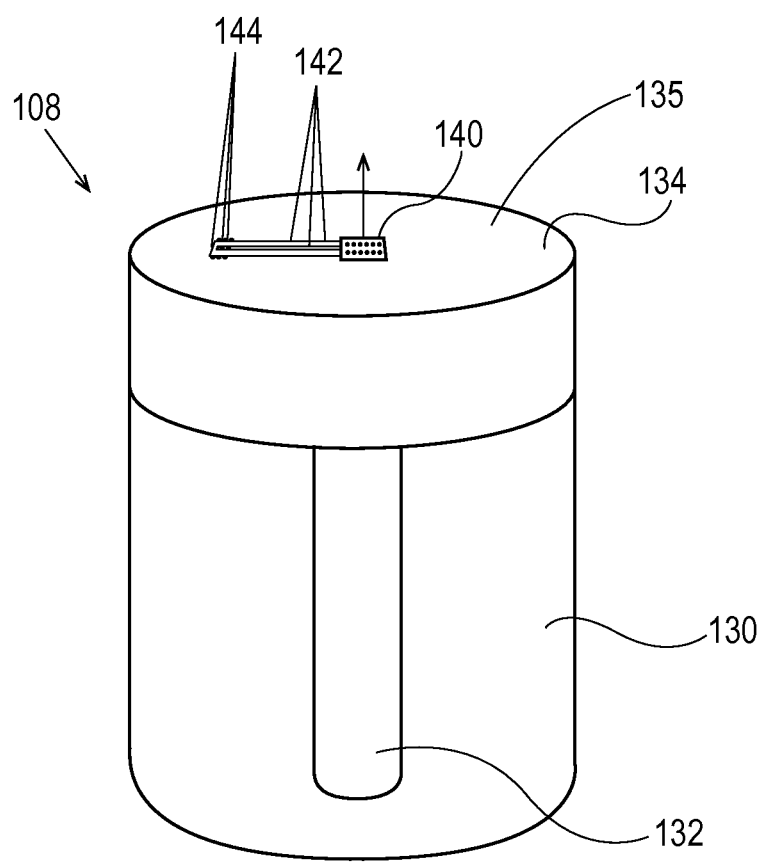
FIG. 10 is a schematic, side elevation view of a refill having a microfluidic delivery member integral with a lid of the refill.

As discussed above and as shown in FIG. 4, the lid 134 comprises a rigid microfluidic delivery member 136. In some exemplary configurations, as shown in FIG. 4, the rigid microfluidic delivery member 136 may be configured as a separate component that is connected with the outer surface 135 of the lid 134. In other exemplary configurations, as shown in FIG. 10, the rigid microfluidic delivery member 136 may be configured as an integral component of the lid 134 and may be disposed on the outer surface 135 of the lid 134.

Figure 11:
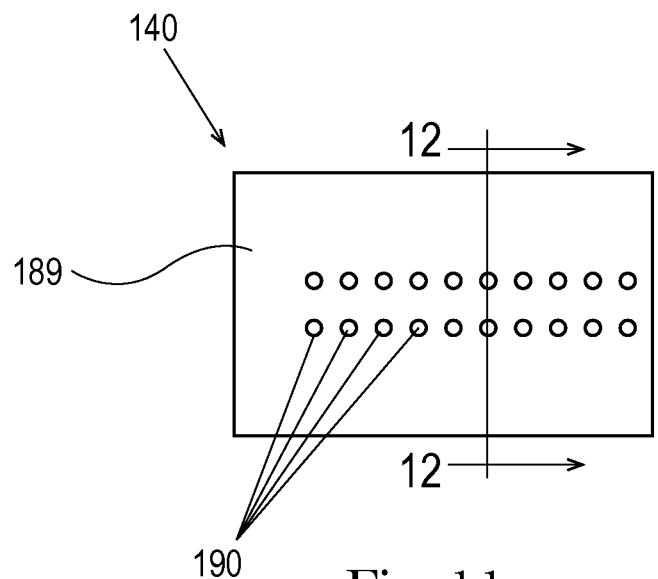
FIG. 11 is a schematic top, plan view of die of a microfluidic delivery member.
Figure 12:
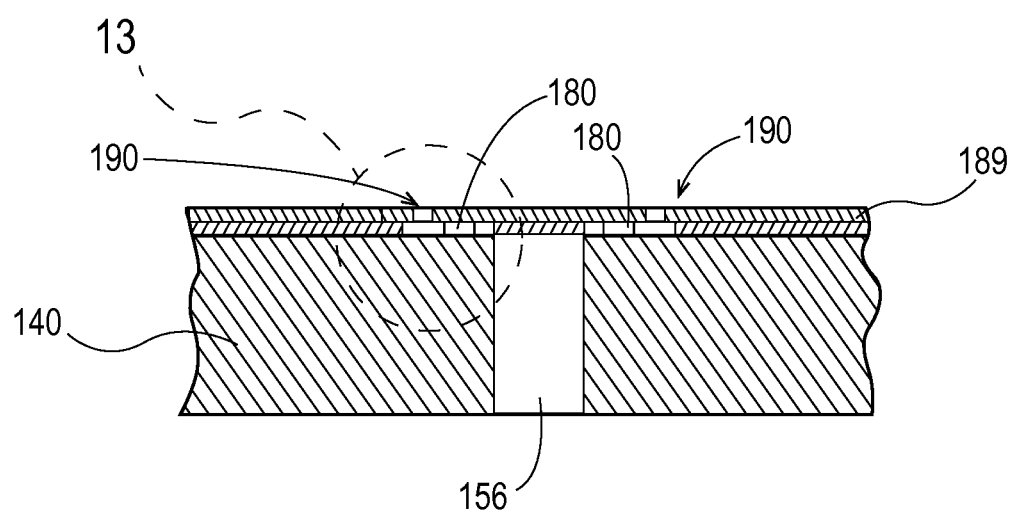
FIG. 12 is a sectional view of the die of FIG. 11 taken along line 12-12.

The microfluidic delivery member 136 includes a die 140 and electrical leads 142 connected with the die 140 that terminate at electrical contacts 144. As shown in FIGS. 11 and 12, the die 140 comprises a fluid channel 156 that is in fluid communication with one or more fluid chambers 180. Each fluid chamber 180 has one or more adjoining walls 182, an inlet 184, and an outlet 186. The inlet 184 of each fluid chamber 180 is in fluid communication with the fluid channel 156 of the die 140 and the outlet 186 of each fluid chamber 180 is in fluid communication with an orifice 190 of a nozzle plate 188. The fluid chambers 180 may be configured to have various different shapes.

Still referring to FIGS. 11 and 12, the die 140 also comprises a nozzle plate 188 comprising one or more orifices 190. In some exemplary configurations, each orifice 190 may be in fluid communication with the outlet 186 of a single fluid chamber 180 such that the fluid composition travels from the fluid chamber 180, through the orifice 190 of the nozzle plate 188 in fluid communication with the fluid chamber 180, and into the air. The nozzle plate 188 may be configured in various different ways. For example, the nozzle may have a thickness $L_N$ of about 10 microns to about 30 microns, or about 20 microns to about 30 microns. The nozzle plate 188 may be composed of various materials. The nozzle plate 188 may be composed of a dry film or liquid photoresist material. Exemplary materials include rigid dry photoresist material such as TMMF, available from Tokyo Ohka Kogyo Co, Ltd of Japan, TMMR, SU-8, and AZ4562.

In some exemplary configurations, the nozzle plate 188 may comprise at least 5 orifices, at least 10 orifices, or at least 20 orifices, or from about 5 to about 30 orifices. The orifices 190 may be configured to have various different shapes. For example, the orifices 190 may be round, square, triangular, or oval. The orifices 190 may be configured to have various different widths $W_O$. The width $W_O$ may be in the range of about 15 microns to about 30 microns. It is to be appreciated that the geometry of the fluid chamber 180 and nozzle plate 188 combine to define the geometry of a drop of fluid composition that is released from the refill 108.

In some exemplary configurations, as shown in FIG. 4, the orifices 190 open in a direction that is perpendicular to, or substantially perpendicular to, the plane that the electrical leads 142 are disposed upon. In some exemplary configurations, the orifices 190 may open at various other angles relative to the plane that the electrical leads 142 are disposed upon.

As shown in FIG. 4, the electrical contacts 144 and the die 140 may be separated by a distance $D_1$. The distance $D_1$ may be in the range of about 5 mm to about 30 mm, or about 15 mm to about 30 mm. It is to be appreciated that the distance $D_1$ allows enough separation between the die 140 and the electrical contacts 144 to prevent the electrical contacts 144 from being contaminated with fluid composition that is released from the refill 108. Moreover, minimizing the distance $D_1$ minimizes the size of the refill 108 while maintaining the die 140 and the electrical contacts 144 disposed on substantially the same plane. Minimizing the size of the refill 108 can decrease the cost of the refill 108.

Figure 13:
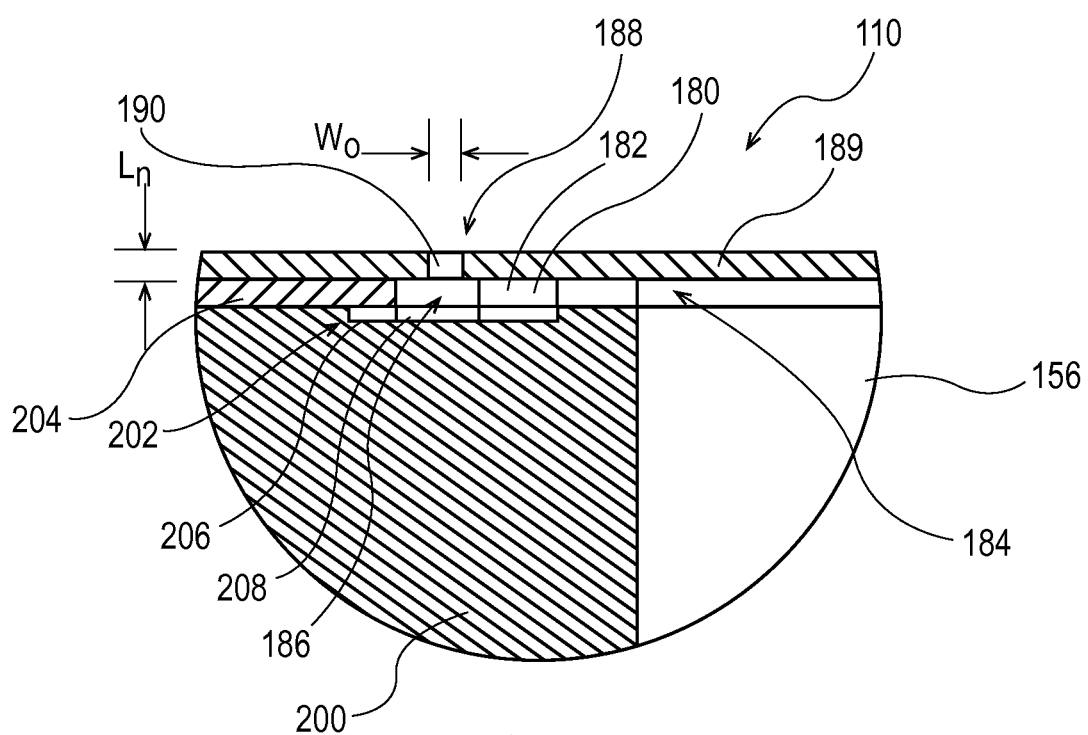
FIG. 13 is a detailed view of portion 13 of FIG. 12.

With reference to FIGS. 4 and 13, in some exemplary configurations, the electrical leads 142 are disposed on only one plane. When the electrical leads 142 are disposed on only one plane, a rigid and inexpensive material may be used for the microfluidic delivery member 136. This is in contrast to a typical inkjet cartridge that has the electrical leads that are disposed on at least two different planes. In addition, the manufacture of a rigid microfluidic delivery member 136 having the electrical leads 142 disposed on only one plane is relatively simple as compared with a flexible member of a typical inkjet refill that is L-shaped in order to separate the electrical contacts and fluid orifice that are located on two different planes.

Figure 14:
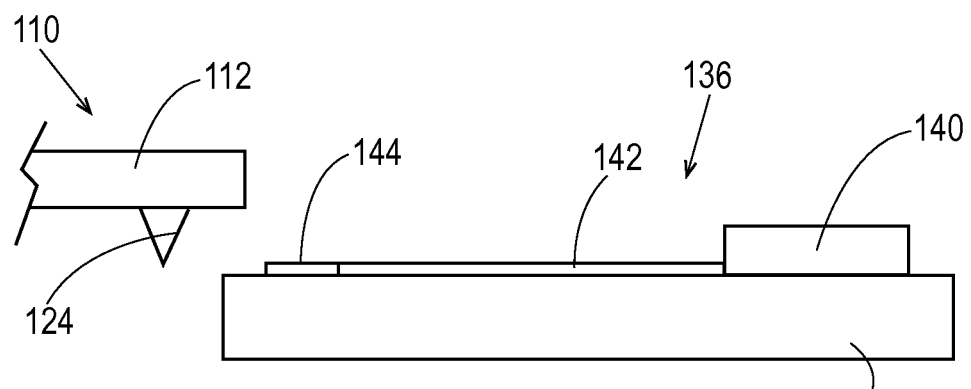
FIG. 14 is a schematic, side elevation view of a microfluidic delivery member and a portion of a holder member.
Figure 15:
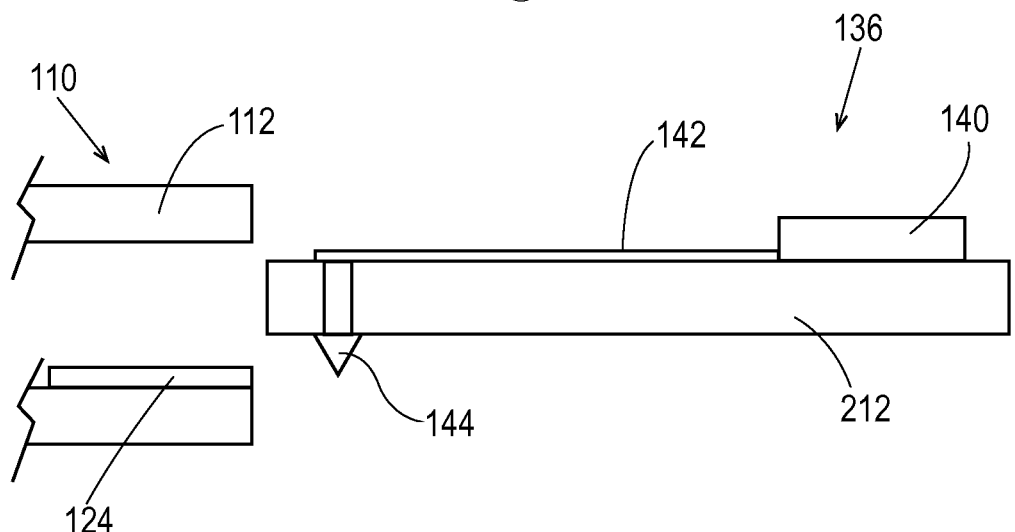
FIG. 15 is a schematic, side elevation view of a microfluidic delivery member and a portion of a holder member.
Figure 16:
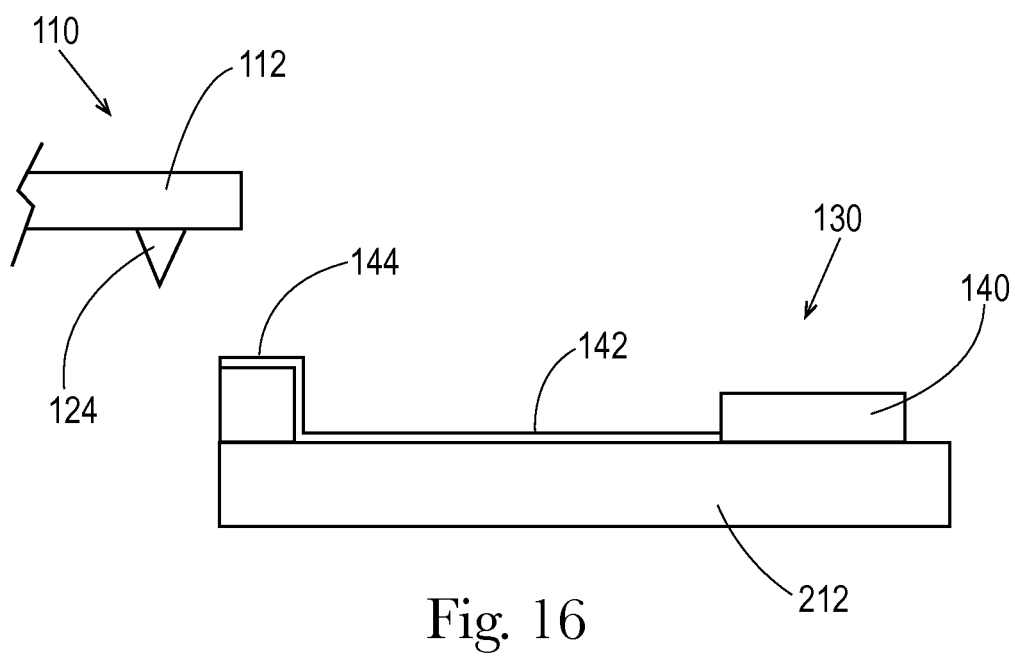
FIG. 16 is a schematic, side elevation view of a microfluidic delivery member and a portion of a holder member.

In some exemplary configurations, as shown in FIGS. 14-16, the electrical contacts 144 and the die 140 are disposed on substantially parallel planes. As used herein, "substantially parallel planes" means that the planes are parallel within 0-10 degrees, or, alternatively, within 0-5 degrees. In some exemplary configurations, the electrical contacts 144 and the die 140 are disposed on the same plane. In such an exemplary configuration, the microfluidic delivery member 136 may be composed of a rigid material that is relatively inexpensive and easy to manufacture. Moreover, in such an exemplary configuration, the refill may be configured to slideably engage with the holder member.

In some exemplary configurations, such as shown in FIG. 15, the die and the electrical contacts may be located on opposite outer surfaces of the microfluidic delivery member. In such an exemplary configuration, the microfluidic delivery member 136 may be composed of a rigid material that is relatively inexpensive and easy to manufacture. Moreover, in such an exemplary configuration, the refill may be configured to slideably engage with the holder member.

Figure 17:
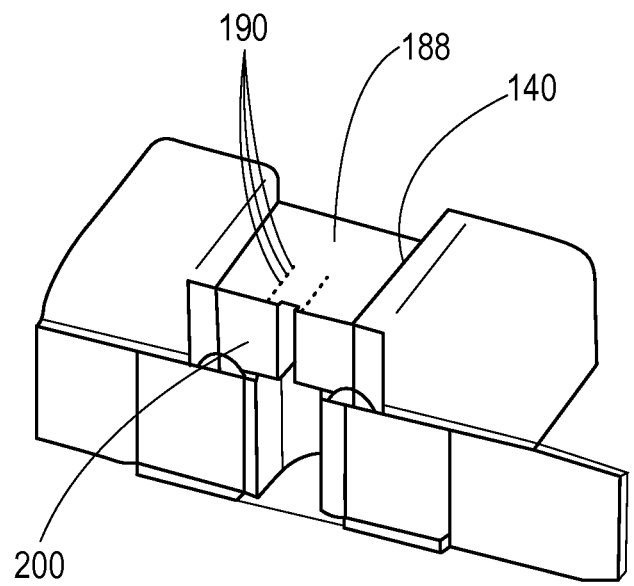
FIG. 17 is a sectional view of the microfluidic delivery member of FIG. 4 taken along line 17-17.

With reference to FIGS. 13 and 17, the die 140 may be comprised of a support substrate 200, conductive layers 202, and one or more polymer layers 204 that define the walls 182 of the fluid chamber 180. The support substrate 200 provides a supporting structure to the conductive and polymer layers 202 and 204, and defines the inlet 184 of the fluid chamber 180. The support substrate 200 may be comprised of various materials, such as silicon or glass. The conductive layers 202 are disposed on the support substrate 200, forming electrical traces 206 with high conductivity and heaters 208 with lower conductivity. Other semi-conductive, conductive, and insulative materials may be deposited to form switching circuits to control electrical signals. A heater 208 may be associated with each fluid chamber 180 of the die 140. The polymer layers 204 are disposed on the conductive layers 202 and define the walls 182 of the fluid chamber 180 and the outlet 186 of the fluid chamber 180. The nozzle plate 188 of the die 140 is disposed on the polymer layers 204.

As discussed above, in some exemplary configurations, the microfluidic delivery member 136, including the die 140 and electrical components, is configured as a separate component that is connected with the lid 134. As shown in FIGS. 3 and 4, in such an exemplary configuration, the microfluidic delivery member 136 may take the form of a printed circuit board 210. The printed circuit board 210 may be a rigid structure.

Figure 18:
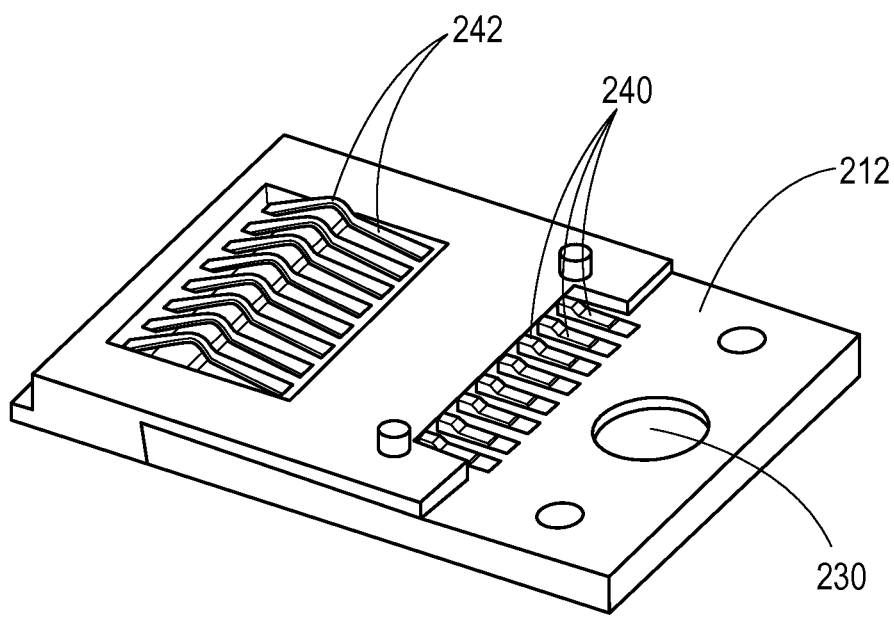
FIG. 18 is a perspective view of a printed circuit board, having an outer covering the printed circuit board removed to show the internal details.

As shown in FIG. 18, the printed circuit board 210 may include a base substrate 212 that is composed of a rigid material such as a fiberglass-epoxy composite substrate material. The printer circuit board 210 may also include conductive layers on top and/or bottom surfaces of the printer circuit board 210. The conductive layers include the electrical leads 142 and electrical contacts 144 and may be composed of a metal material such as copper.

Figure 19:
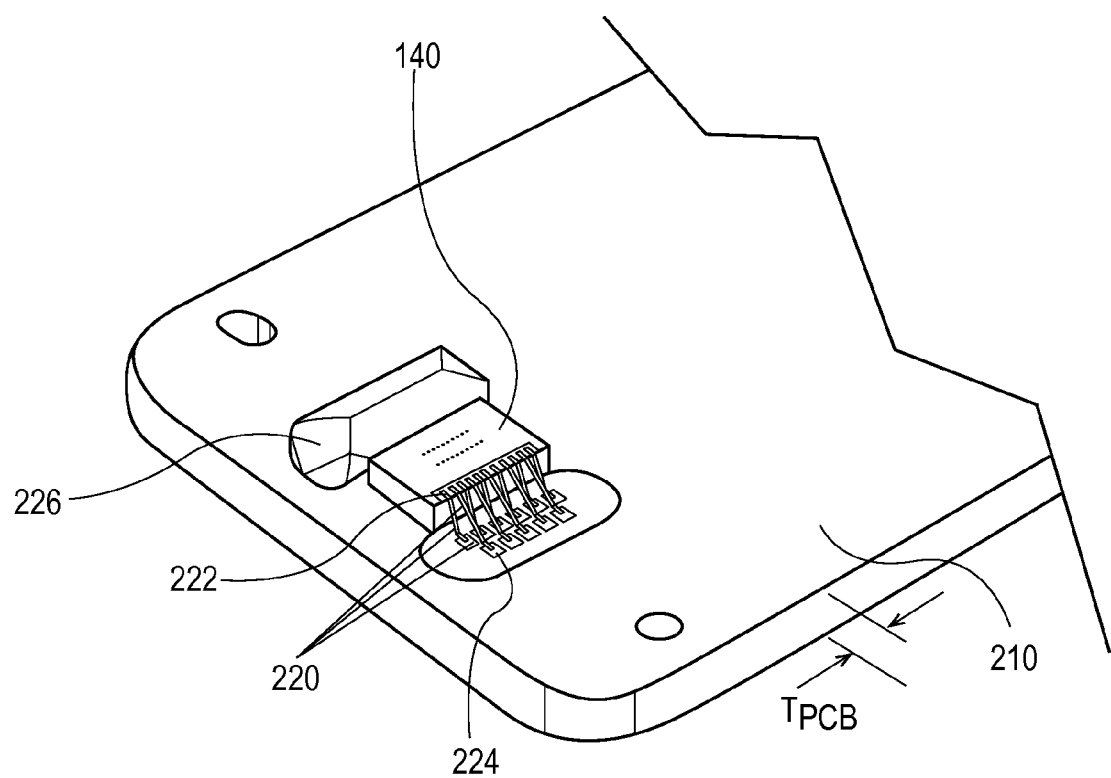
FIG. 19 is a perspective view of a printed circuit board, having portions removed to show details of the electrical connections.

With reference to FIG. 19, the die 140 may be attached to the printed circuit board 210 through the use of adhesive, such as an epoxy adhesive. The electrical connection from the die 140 to the printed circuit board 210 may be established by a wire bonding process, where small wires 220 are thermally attached to bond pads 222 on the die 140 and to corresponding bond pads 224 on the printed circuit board 210. The small wires 220 may be composed of gold or aluminum, for example. An encapsulant material 226, such as an epoxy compound, may be applied to the bonded areas between the wires 220 and the bond pads 222 and 224 to protect the delicate connections from mechanical damage and other environmental effects.

The conductive layers are arranged into conductive paths through an etching process. The conductive paths are protected from mechanical damage and other environmental effects in most areas of the printed circuit board 210 by a photo-curable polymer layer 204, often referred to in the industry as a soldermask layer. In selected areas, such as the fluid composition flow paths and bond pads 222 and 224, the conductive copper paths may be protected by an inert metal coating such as gold. Other material choices could be tin, silver, or other low reactivity, high conductivity metals.

The inert metal coating in the fluid paths protects the printed circuit board 210 from potential damage from the fluid composition. Since it is necessary for the fluid composition to pass through the printed circuit board 210 to the die 140, the fluid composition may cause degradation of more reactive metals such as copper, or metal ions or products of metal-fluid chemical reactions could degrade the fluid composition without the use of the inert metal coating. Further, since the base substrate 212 could be susceptible to migration of the fluid composition, the inert metal coatings of the fluid flow paths contain the fluid composition within the desired flow path.

As shown in FIG. 19, the printed circuit board 210 may have various thicknesses $T_{PCB}$. The thickness $T_{PCB}$ of the printed circuit board 210 may be between about 0.8 mm and about 1.6 mm thick. Printed circuit boards 210 may have conductive layers on one or both sides, or, the printed circuit board can be constructed in layers to incorporate four or more conductive layers. In printed circuit boards 210, connectivity between conductive layers is achieved by holes or slots which have been clad in metal through an electroplating process. Such holes or slots are often termed vias. In some exemplary configurations, the rigid printed circuit board 210 is of the two-layer type, with a plated slot 230 located under the die 140. The plated slot 230 forms the fluid path to the die 140, and the metal plating forms an impermeable barrier.

As shown in FIG. 10, in other exemplary configurations, the microfluidic delivery member 136 may be integrally formed with the lid 134. In such a configuration, the die 140, electrical leads 142, and electrical contacts 144 are connected directly with the lid 134, instead of being attached to the lid 134 as a separate component. In such an exemplary configuration, the rigid material of the lid 134 helps to provide strong electrical connection between the refill 108 and the holder member 110.

Figure 7B:
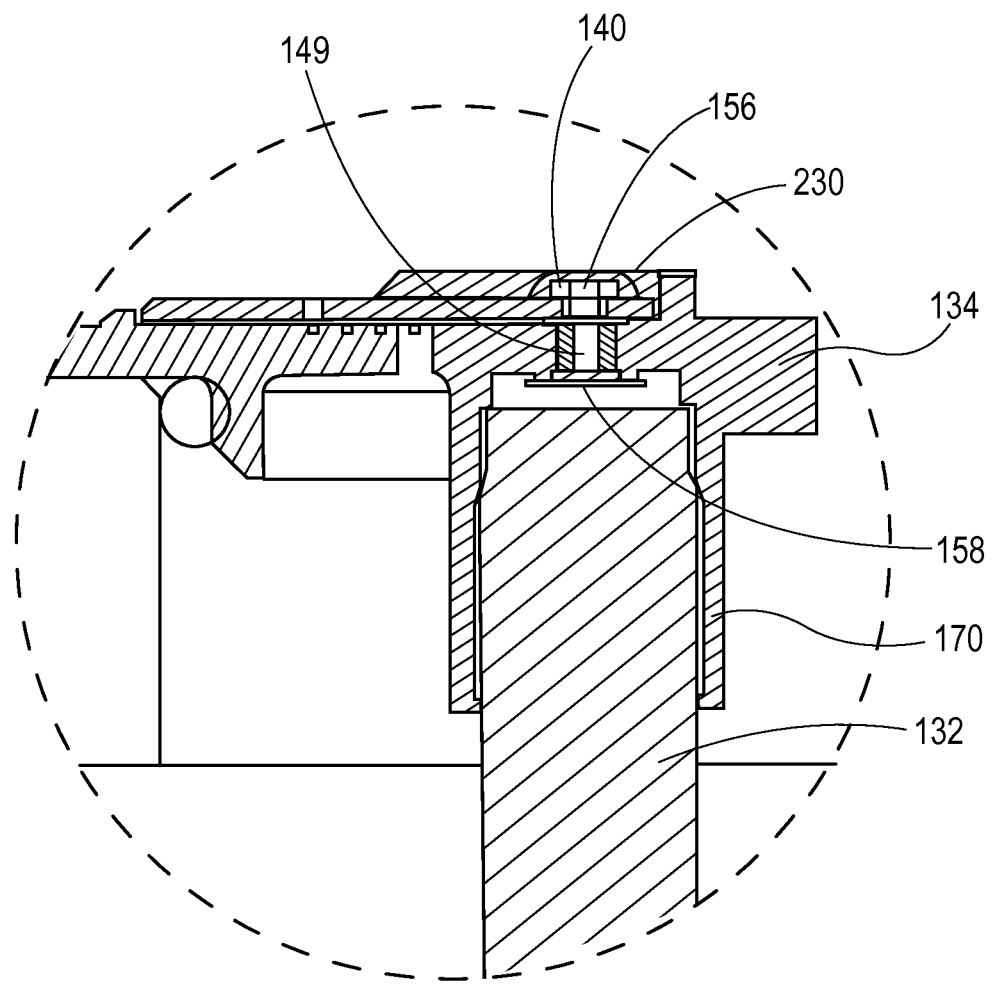
FIG. 7B is a detailed view of portion 7B of FIG. 7A.

With reference to FIGS. 7A, 7B, and 13, the fluid composition travels in a fluid path from the reservoir 130, through the transport member 132, through the filter 158, through the aperture 149 in the lid 134, into the die 140, and into the air. The refill 108 functions by balancing capillary effects in the die 140 and the transport member 132. It is to be appreciated that the die 140 has the smallest fluid passages in the fluid path, and, therefore, can produce the highest capillary pressures in the fluid path. Conversely, the transport member 132 is configured to have a lower capillary pressure than the die 140 such that the fluid composition preferentially flows from the transport member 132 to the die 140. The transport member 132 may be selected to have a relatively small porosity and high capillary pressure to aid in the process of priming the refill 108, as will be discussed in more detail below. However, in order to maintain priming of the refill 108, it is to be appreciated that the gauge pressure of the fluid composition (with respect to the surroundings) at the die 140 and at the transport member 132, taking into account the highest hydrostatic column pressure from the die 140 to the free surface of the fluid composition, cannot be less than the maximum capillary pressure capable of being sustained at the orifices.

The transport member 132 provides a fluid pressure at the die 140 that is slightly below atmospheric pressure. The fluid pressure at the die 140 is measured as the hydrostatic column pressure measured from the interface of the transport member 132 and the die 140 to the free surface of the fluid composition in which the transport member 132 is partially immersed. Having the fluid composition within the die 140 slightly below atmospheric pressure prevents the fluid composition from flowing out of the orifices 190 under the influence of hydrostatic pressure or interfacial wetting.

Figure 20:
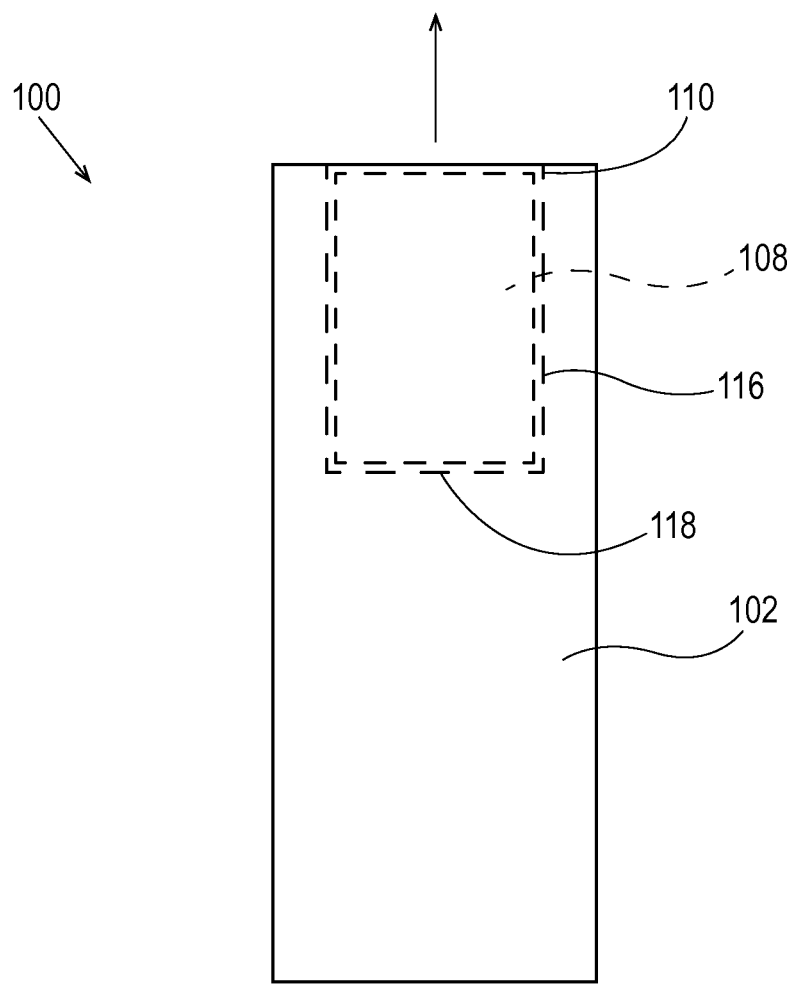
FIG. 20 is a schematic, side elevation view of a microfluidic delivery system having a refill with a flat, horizontally oriented top wall of a lid.

The holder member 110 may be configured in various ways. For example, as shown in FIGS. 1 and 2, the holder member 110 may comprise a top wall 112, a bottom wall 114 opposing the top wall 112, and/or a side wall 116 extending between the top and bottom walls 112 and 114. In other exemplary configurations, as shown in FIG. 20, the holder member 110 may include one or more side walls 116 and a bottom wall 114. The side wall or walls 116 and bottom wall 114 may be integrally formed.

Figure 21:
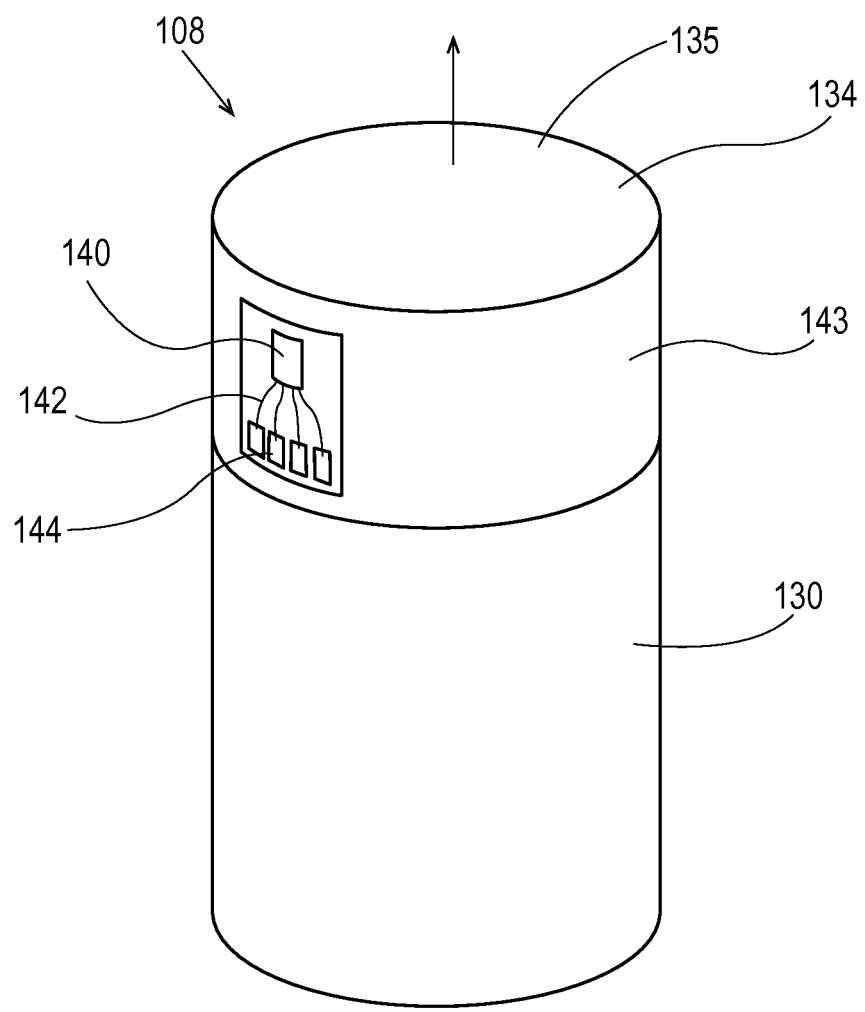
FIG. 21 is a schematic, perspective view of a refill having a microfluidic delivery member connected with a side wall of a lid.

The microfluidic delivery member 136 may be disposed in various locations on the lid 134 of the refill 108. For example, as shown in FIG. 7A, the microfluidic delivery member 136 may be disposed on a top wall 141 of the lid 134. In other exemplary configurations, such as shown in FIG. 21, the microfluidic delivery member may be disposed on a side wall 143 of the lid 134.

The lid may be configured in various different ways. For example, In some exemplary configurations, such as shown in FIG. 3, the top wall 141 of the lid 134 may be arranged in a substantially flat and horizontal orientation. In such an exemplary configuration, the microfluidic delivery member 136 may be disposed in a substantially flat and horizontal orientation. In such an exemplary configuration, the fluid composition may release in an upward direction at an angle θ that is about 90 degrees relative to horizontal.

Figure 22:
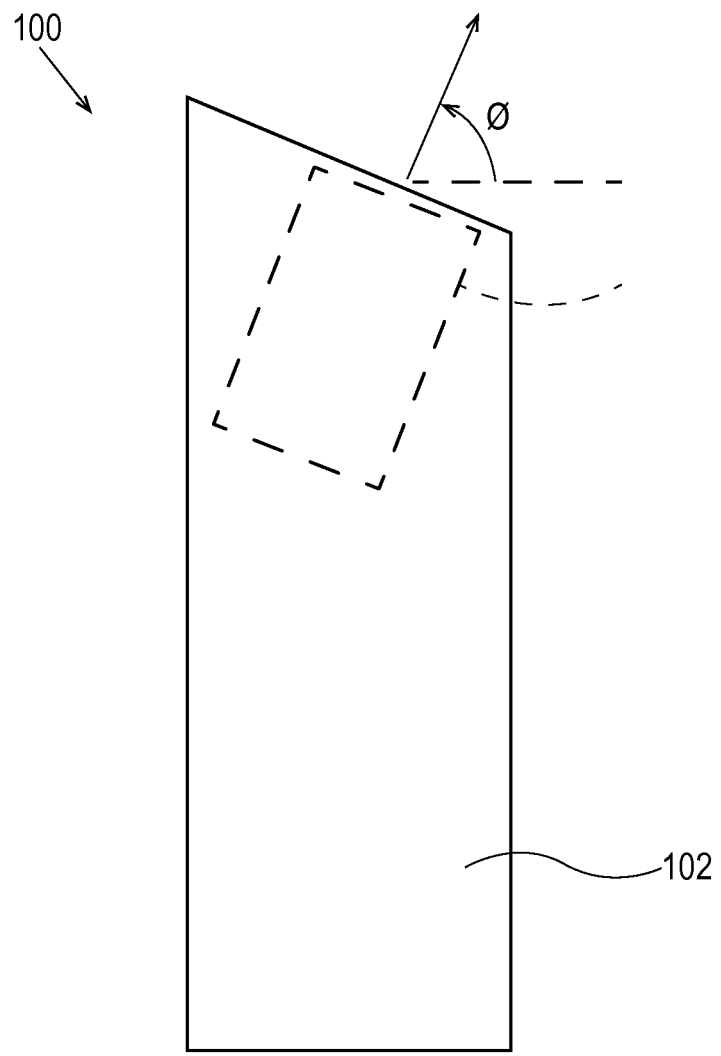
FIG. 22 is a schematic, side elevation view of a microfluidic delivery system having a refill disposed at an angle.
Figure 23:
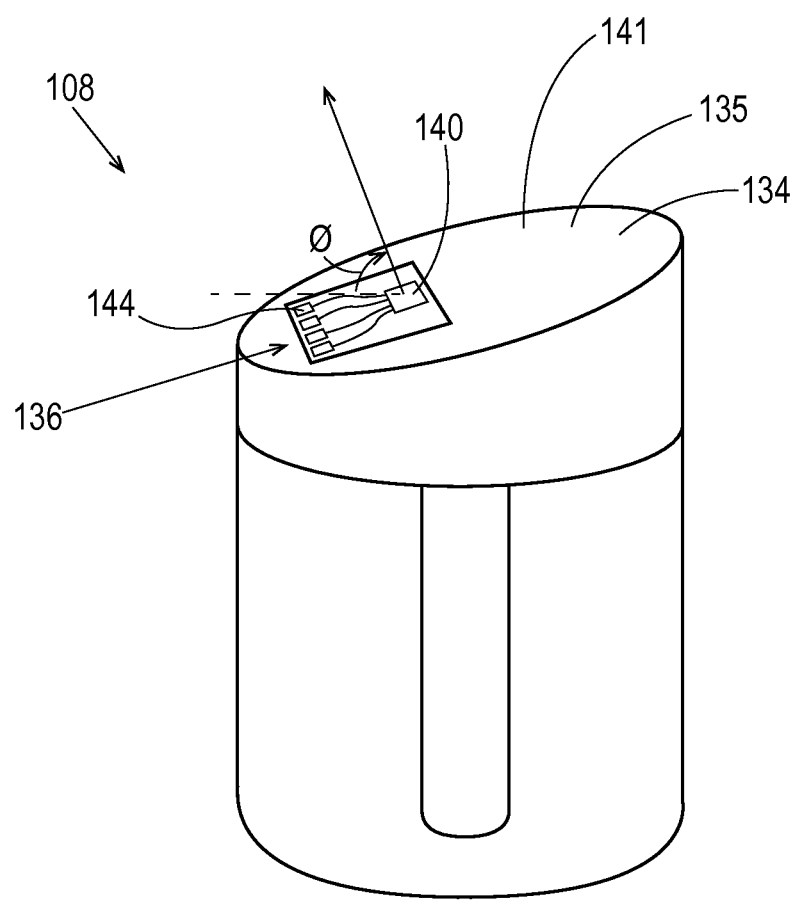
FIG. 23 is a schematic, perspective view of a refill having a lid with an angled top wall.
Figure 24:
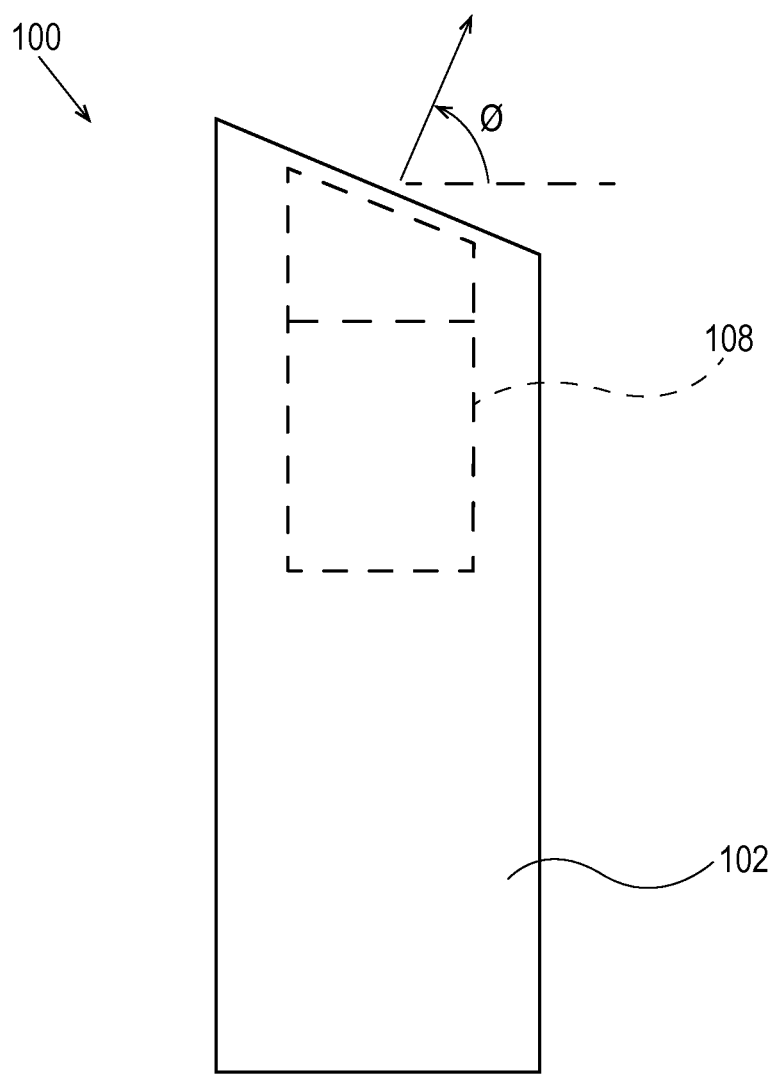
FIG. 24 is a schematic, side elevation view of a microfluidic delivery system having a refill with an angled top wall of a lid.
Figure 25:
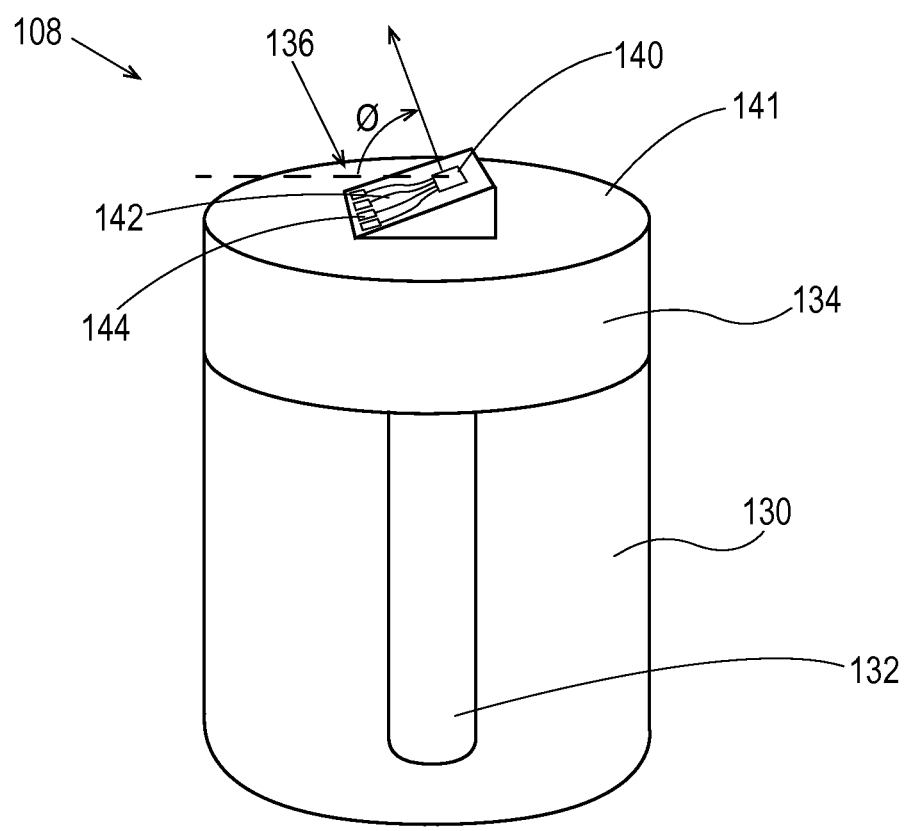
FIG. 25 is a schematic, perspective view of a refill having a microfluidic delivery member disposed at an angle relative to a top wall of a lid.

In some exemplary configurations, such as shown in FIG. 22, the refill 108 may be disposed at an angle θ in the housing 102 such that the fluid composition releases at an angle between zero degrees and 90 degrees from horizontal. In other exemplary configurations, such as shown in FIGS. 23 and 24, the wall of the lid 134 that the microfluidic delivery member is disposed on, shown as the top wall 141 of the lid 134 in FIGS. 23 and 24 for exemplary purposes only, may be angled, and, thus, the microfluidic delivery member 136 may be disposed at an angle. In such an exemplary configuration, the fluid composition may release at an angle θ between zero and 90 degrees relative to horizontal. In other exemplary configurations, such as shown in FIG. 25, the lid 134 may be flat and substantially horizontally oriented, while the microfluidic delivery member 136 may be disposed at an angle relative to the wall of the lid 134 that the microfluidic delivery member 136 is disposed on, shown as the top wall 141 of the lid 134 for exemplary purposes only. In such an exemplary configuration, the fluid composition may release at an angle θ between zero and 90 degrees relative to horizontal.

The fluid composition may be released at various angles from the microfluidic delivery system. In some exemplary configurations, it may be desired to release the fluid composition in a direction that is between zero and 90 degrees from horizontal. For example, the fluid composition may be released in a direction that is between about 40 degrees and about 75 degrees from horizontal. Without wishing to be bound by theory, it is believed that releasing the fluid composition in a direction that is between about 40 and about 75 degrees from horizontal minimizes the amount of fluid composition that falls onto the housing 102 and/or onto a surface such as a table or floor. That is, releasing the fluid composition at an angle of 90 degrees from horizontal may result in deposition of a portion of the fluid composition onto the microfluidic delivery system. Likewise, releasing the fluid composition at an angle of zero degrees from horizontal may result in deposition of a portion of the fluid composition onto the surface below, such as a floor, countertop, or table.

Figure 26:
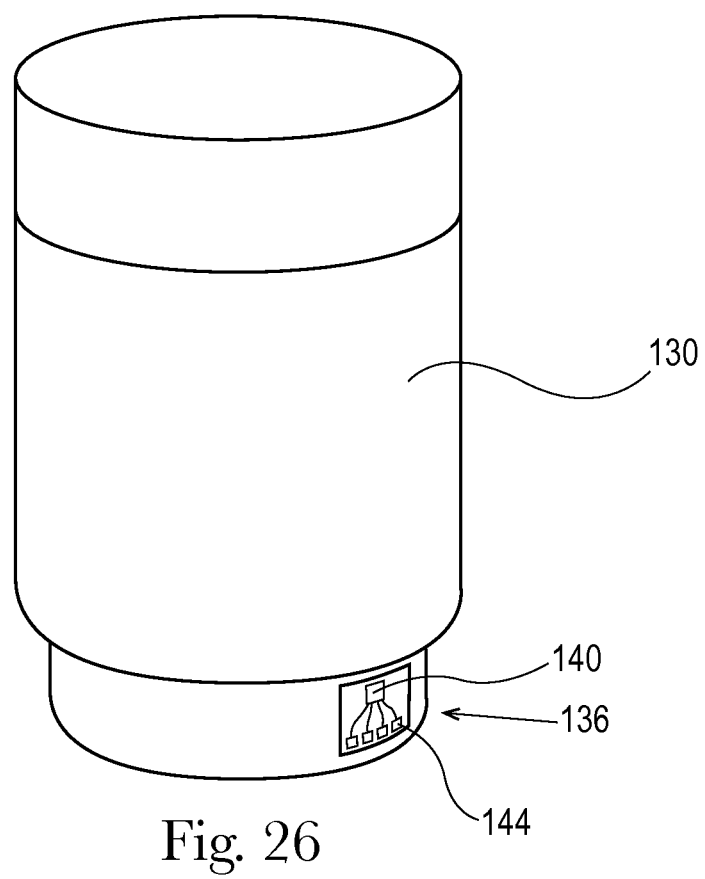
FIG. 26 is a schematic, perspective view of a refill that is configured to deliver a fluid composition to a die in a direction parallel with the force of gravity.
Figure 27:
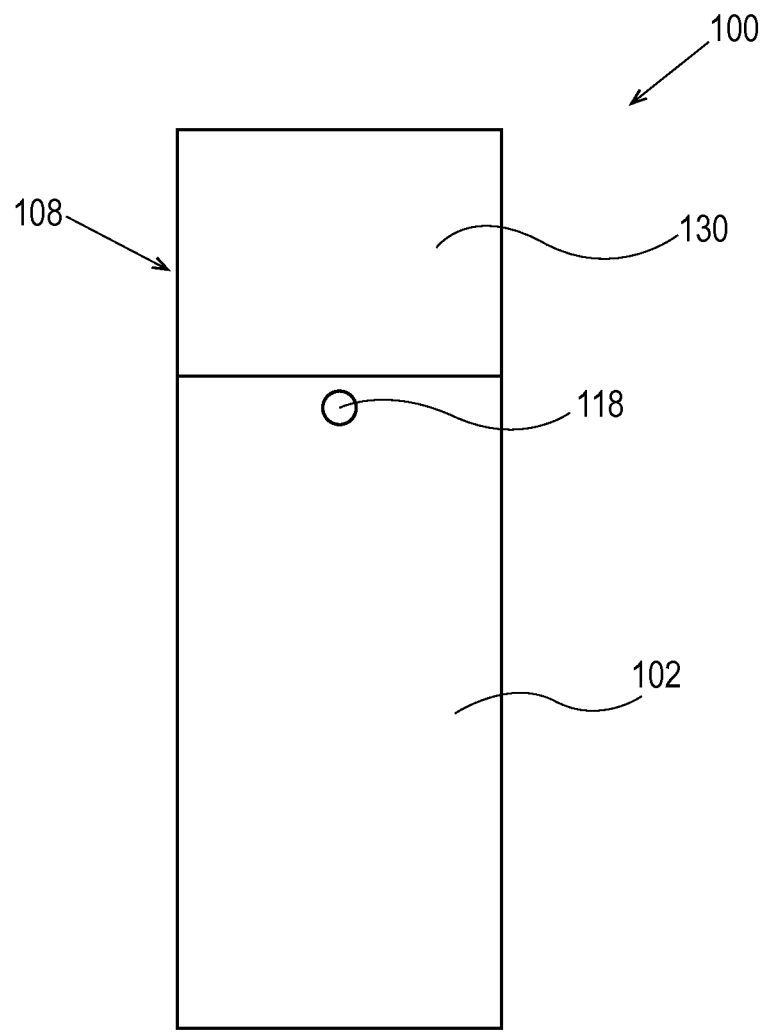
FIG. 27 is a schematic, side elevation view of a microfluidic delivery system having a refill that is configured to deliver a fluid composition to a die in a direction parallel with the force of gravity.

While it is shown in FIGS. 3 and 7A that the transport member 132 may transport the fluid composition up, against the force of gravity, it is to be appreciated that in some exemplary configurations, such as shown in FIGS. 26 and 27, the refill 108 may be configured such that the fluid composition is fed to the die 140 in the same direction as the force of gravity acting on the fluid composition. In such an exemplary configuration, the refill 108 may comprise a porous structure to control the release of fluid composition from the die 140.

Figure 28:
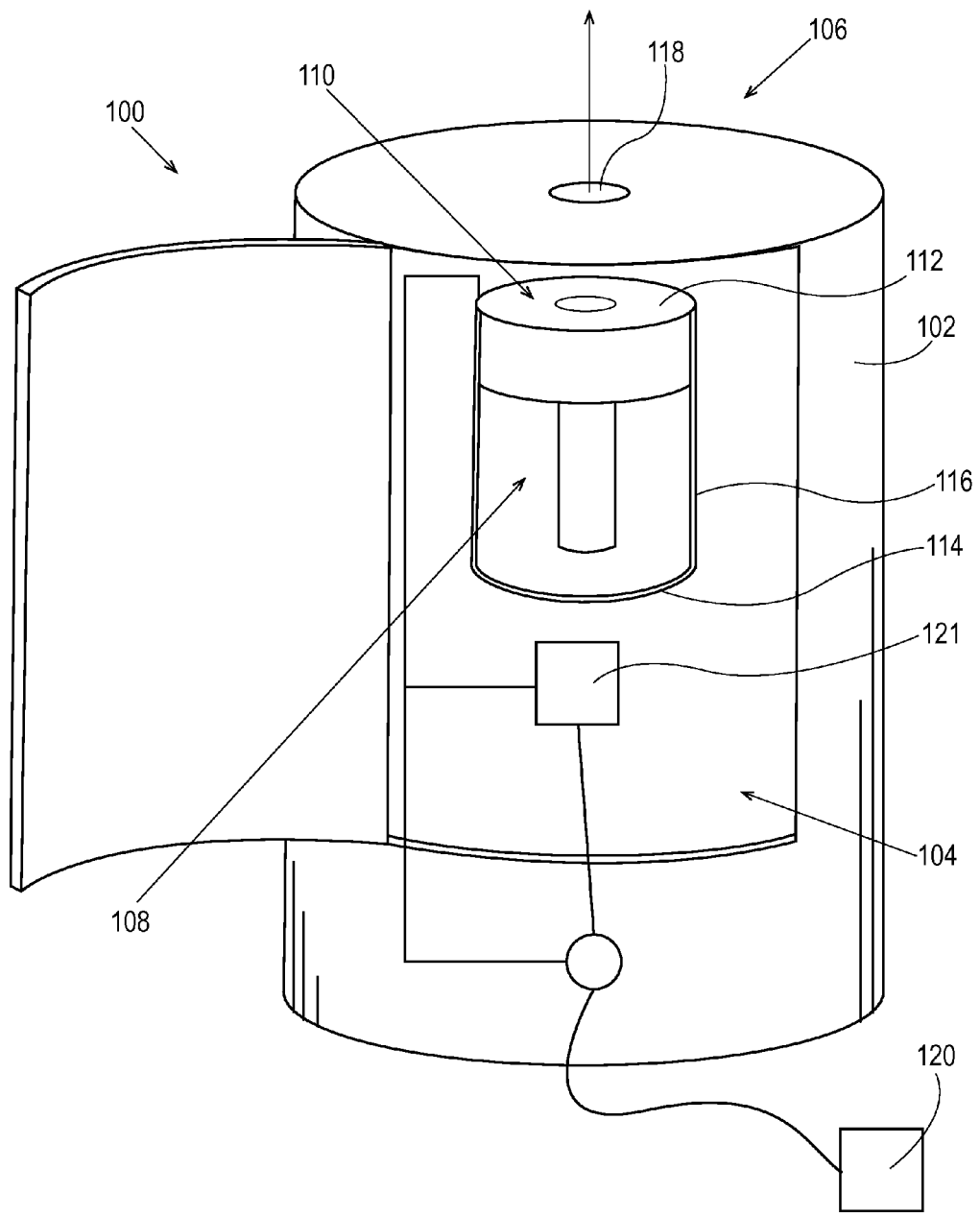
FIG. 28 is a schematic, side elevation view of a microfluidic delivery system configured with battery-power.

As discussed above, the microfluidic delivery system 100 includes a power source 120. The microfluidic delivery system 100 may be powered by an AC outlet, as shown FIG. 1. Or, in other exemplary configurations, the microfluidic delivery system 100 may be powered by battery-power 121 as shown in FIG. 28. In such an exemplary configuration, the battery-power 121 may be recharcheable using a power source 120.

Priming the Refill

As previously mentioned, the refill 108 of the microfluidic delivery system 100 is primed before inserting the refill 108 into the housing 102. The refill 108 is primed by removing any air from the transport member 132, the aperture 149, the filter 158, the lid 134, the slot 230 of the printed circuit board 210 (if present) and the die 140. In some exemplary configurations, the nozzles may be sealed after priming to prevent de-priming of the refill 108 or evaporative loss of the fluid composition prior to the refill 108 being inserted into the housing of the microfluidic delivery system 100.

Operation of the Microfluidic Delivery System

Figure 29:
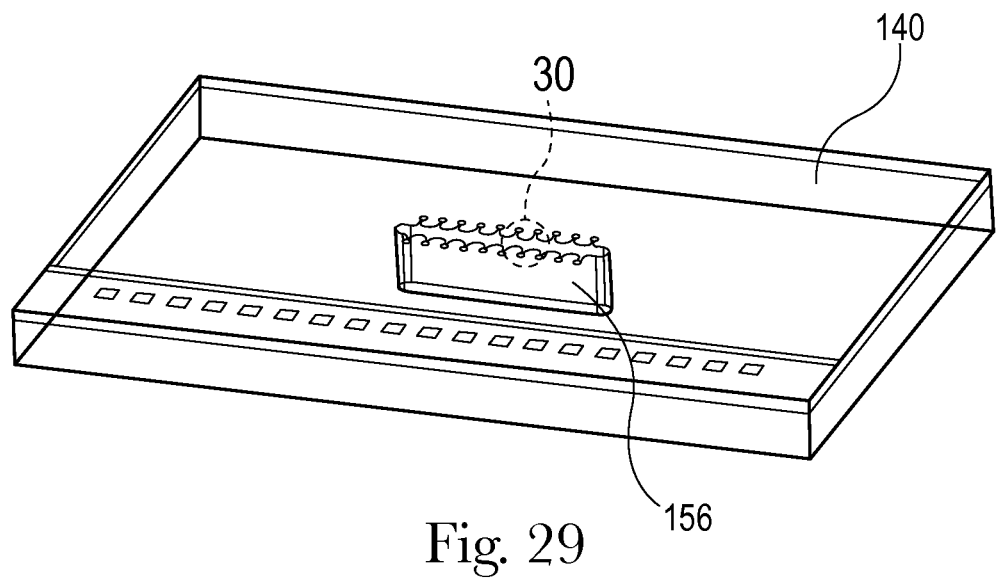
FIG. 29 is a perspective view of a die showing the fluid channel, fluid chambers, and orifices of the die.
Figure 30:
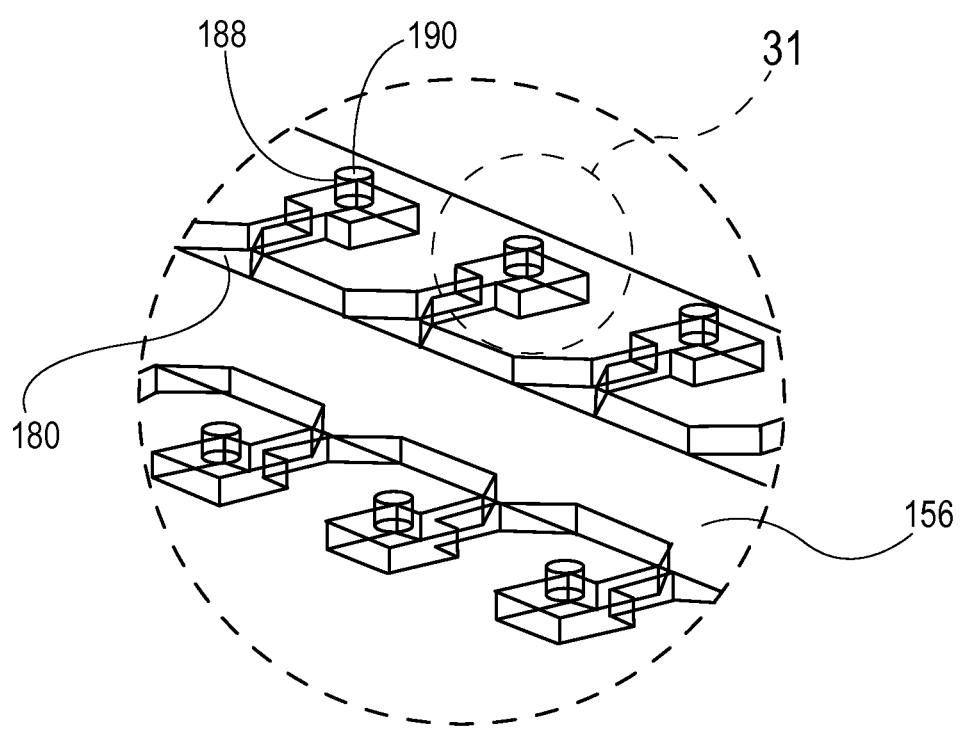
FIG. 30 is a detailed view of portion 30 of the die of FIG. 29.
Figure 31:
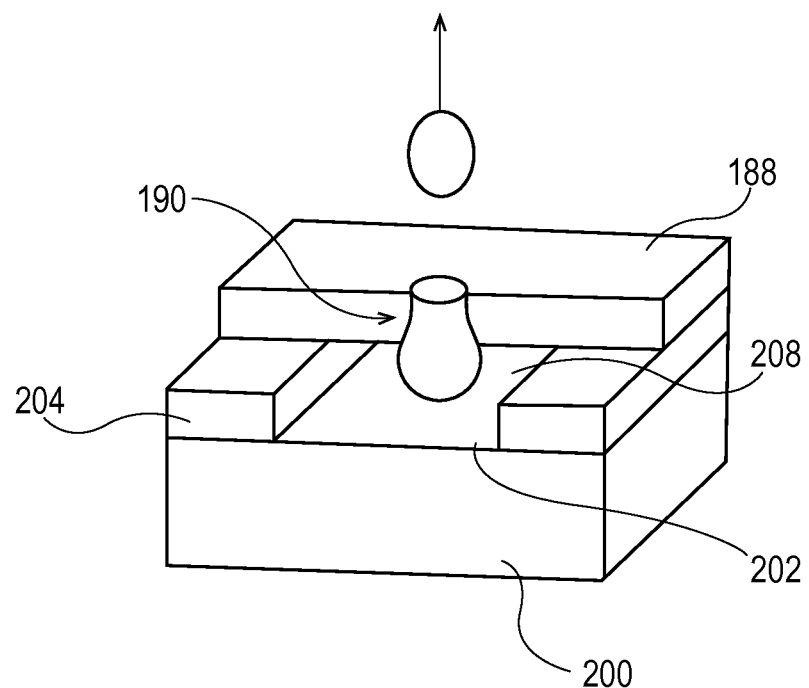
FIG. 31 is a detailed view of portion 31 of the die of FIG. 30.

As previously mentioned, the microfluidic delivery system 100 may deliver a fluid composition 122 from the refill 108 using thermal heating. With reference to FIGS. 1, 3, 7A, 10, and 13, in operation, fluid composition 122 contained within the reservoir 130 wicks up the transport member 132 toward the lid 134 using capillary force. After passing through the second end portion 162 of the transport member 132, the fluid composition 122 travels through the filter 158, if present, through the aperture 149 in the lid 134, and into the die 140. As shown in FIG. 29-31, the fluid composition 122 travels through the fluid channel 156 and into the inlet 184 of each fluid chamber 180. The fluid composition 122, which is comprised in part by a volatile component, travels through each fluid chamber 180 to the heater 208 of each fluid chamber 180. It is to be appreciated that portions of the die 140 in FIG. 31 are removed to more clearly illustrate movement of a droplet of fluid composition through the die 140.

As shown in FIG. 31, the heater 208 vaporizes at least a portion of the volatile components in the fluid composition 122, causing a vapor bubble form. The vapor bubble forces a droplet of fluid composition 122 through the orifice 190 of the nozzle plate 188. Next, the vapor bubble collapses and causes the droplet of fluid composition 122 to break away and release from the orifice 190. The droplet of fluid composition travels through the aperture 126 in the holder member 110, through the aperture 118 in the housing 102, and into the air. Fluid composition 122 then refills the fluid chamber 180 and the process may be repeated to release additional droplets of fluid composition 122.

The timing between releases of droplets of fluid composition 122 from the microfluidic delivery system may be varied. The flow rate of fluid composition released from the microfluidic delivery system 100 may be varied. For example, the microfluidic delivery system 100 may be configured to deliver a fluid composition 122, such as a perfume composition, to rooms of various sizes. As such, the flow rate may be adjusted to account for the size of the room. Moreover, in the case of a perfume composition, the flow rate may be adjusted depending upon the user's preference in scent intensity. In some exemplary configurations, the flow rate of fluid composition 122 released from the refill 108 may be in the range of about 5 to about 40 mg/hour.

Refilling the System

Once a refill 108 is spent of fluid composition, the spent refill 108 may be removed from the holder member 110 of the housing 102 and a new refill 108 may be inserted into the housing 102. In some exemplary configurations, the refill 108 is inserted into the housing 102 in a direction that is parallel with the plane that the electrical leads are disposed upon. With reference to FIG. 1, in some exemplary configurations, the refill 108 is inserted into the housing in a direction that is normal to the firing direction of the microfluidic delivery member 136 and parallel to the plane that the die 140 and electrical contacts 144 upon.

In some exemplary configurations, the refill 108 is inserted and removed from the holder member 110 of the housing by sliding the refill 108 relative to the holder member 110. With reference to FIGS. 1 and 2, in some exemplary configurations, the refill 108 may slide into the housing in a left-to-right or right-to-left motion. With reference to FIGS. 26 and 27, in other exemplary configurations, the refill 108 may slide into the housing in an upward or downward motion. For example, with reference to FIG. 2, in some exemplary configurations, the refill 108 is connected with the housing by sliding the refill 108 into the holder member 110 such that the reservoir 130 of the refill 108 connects with the bottom and side walls 114 and 116 of the holder member 110 and the lid 134 of the refill 108 connects with the top wall 112 of the holder member 110. As shown in FIG. 27, in some exemplary configurations, the refill 108 may provide a continuous outer surface to the housing 102. In such an exemplary configuration, the housing 102 may not comprise a door.

It is to be appreciated that the refill 108 may be connected with the holder member 110 in various ways. For example, the refill 108 may be spring-loaded with the holder member 110, and, may have a release button to release the refill 108 from the holder member 110. In other exemplary configurations, the refill 108 may engage with a fastener to secure the refill 108 into the holder member 110.

When the electrical contacts 144 are arranged parallel with the direction of insertion of the refill 108, the engagement of the electrical contacts 124 of the holder member 110 with the electrical contacts 144 on the refill 108 may cause abrasion to the electrical contacts 144 of the refill 108, which can remove oxides and other contaminants from the surfaces of the electrical contacts 144. As a result, the quality of electrical connection between the refill 108 and the housing 102 may be improved or maintained over time. Moreover, the rigidity of the microfluidic delivery member 136 provides a relatively strong electrical connection between the refill 108 and the housing 102.

Fan

In some exemplary configurations, the microfluidic delivery system may comprise a fan to assist in driving room-fill and to help avoid deposition of larger droplets from landing on surrounding surfaces that could damage the surface. The fan may be any known fan, such as a 5V 25×25×5 mm DC axial fan (Series 250, Type255N from EBMPAPST), used in the art for air freshening systems that delivers 1-1000 cubic centimeters of air/minute, alternatively 10-100 cubic centimeters/minute.

Sensors

In some exemplary configurations, the microfluidic delivery system may include commercially available sensors that respond to environmental stimuli such as light, noise, motion, and/or odor levels in the air. For example, the microfluidic delivery system can be programmed to turn on when it senses light, and/or to turn off when it senses no light. In another example, the microfluidic delivery system can turn on when the sensor senses a person moving into the vicinity of the sensor. Sensors may also be used to monitor the odor levels in the air. The odor sensor can be used to turn-on the microfluidic delivery system, increase the heat or fan speed, and/or step-up the delivery of the fluid composition from the microfluidic delivery system when it is needed.

The sensor may also be used to measure fluid levels in the reservoir or count firing of the heating elements to indicate the refill's end-of-life in advance of depletion. In such case, an LED light may turn on to indicate the refill needs to be filled or replaced with a new refill.

The sensors may be integral with the housing or in a remote location (i.e. physically separated from the delivery system housing) such as remote computer or mobile smart device/phone. The sensors may communicate with the delivery system remotely via low energy blue tooth, 6 low pan radios or any other means of wirelessly communicating with a device and/or a controller (e.g. smart phone or computer).

Fluid Composition

The fluid composition of the present disclosure may exhibit a viscosity at 20° C. of less than 20 centipoise ("cps"), alternatively less than 18 cps, alternatively less than 16 cps, alternatively from about 5 cps to about 16 cps, alternatively about 8 cps to about 15 cps. And, the volatile composition may have surface tensions below about 35, alternatively from about 20 to about 30 dynes per centimeter. Viscosity is in cps, as determined using the Bohlin CVO Rheometer system in conjunction with a high sensitivity double gap geometry.

In some embodiments, the fluid composition is free of suspended solids or solid particles existing in a mixture wherein particulate matter is dispersed within a liquid matrix. Free of suspended solids is distinguishable from dissolved solids that are characteristic of some perfume materials.

The fluid composition of the present invention comprises a perfume composition present in an amount greater than about 50%, by weight of the fluid composition, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%. In some embodiments, the fluid composition may consist entirely of the perfume composition (i.e. 100 wt. %).

The perfume composition may contain one or more perfume materials. The perfume materials are selected based on the material's boiling point ("B.P."). The B.P. referred to herein is measured under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969.

In the present invention, the perfume composition may have a B.P. of less than 250° C., alternatively less than 225° C., alternatively less than 200° C., alternatively less than about 150° C., alternatively less than about 120° C., alternatively less than about 100° C., alternatively about 50° C. to about 200° C., alternatively about 110° C. to about 140° C. Table 1 lists some non-limiting, exemplary individual perfume materials suitable for the perfume composition of the present invention.

TABLE 1

| CAS Number | Perfume Raw Material Name | B.P. (° C.) |
|---|---|---|
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 470-82-6 | Eucalyptol | 175 |
| 141-78-6 | Ethyl acetate | 77 |

Table 2 shows an exemplary perfume composition having a total B.P. less than 200° C.

TABLE 2

| CAS Number | Perfume Raw Material Name | Wt % | B.P. (° C.) |
|---|---|---|---|
| 123-68-2 | Allyl Caproate | 2.50 | 185 |
| 140-11-4 | Benzyl Acetate | 3.00 | 214 |
| 928-96-1 | Beta Gamma Hexenol | 9.00 | 157 |
| 18479-58-8 | Dihydro Myrcenol | 5.00 | 198 |
| 39255-32-8 | Ethyl 2 Methyl Pentanoate | 9.00 | 157 |
| 77-83-8 | Ethyl Methyl Phenyl Glycidate | 2.00 | 260 |
| 7452-79-1 | Ethyl-2-Methyl Butyrate | 8.00 | 132 |
| 142-92-7 | Hexyl Acetate | 12.50 | 146 |
| 68514-75-0 | Orange Phase Oil 25X1.18%-Low Cit. 14638 | 10.00 | 177 |
| 93-58-3 | Methyl Benzoate | 0.50 | 200 |
| 104-93-8 | Para Cresyl Methyl Ether | 0.20 | 176 |
| 1191-16-8 | Prenyl Acetate | 8.00 | 145 |
| 88-41-5 | Verdox | 3.00 | 223 |
| 58430-94-7 | Iso Nonyl Acetate | 27.30 | 225 |
| | TOTAL: | 100.00 | |

When formulating fluid compositions for the present invention, one may also include solvents, diluents, extenders, fixatives, thickeners, or the like. Non-limiting examples of these materials are ethyl alcohol, carbitol, diethylene glycol, dipropylene glycol, diethyl phthalate, triethyl citrate, isopropyl myristate, ethyl cellulose, and benzyl benzoate.

In some embodiments, the fluid composition may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs of the present invention aid in the evaporation of perfume materials and may provide a hedonic, fragrance benefit. FPCs may be used in relatively large concentrations without negatively impacting perfume character of the overall composition. As such, in some embodiments, the fluid composition of the present invention may be substantially free of VOCs, meaning it has no more than 18%, alternatively no more than 6%, alternatively no more than 5%, alternatively no more than 1%, alternatively no more than 0.5%, by weight of the composition, of VOCs. The volatile composition, in some embodiments, may be free of VOCs.

Perfume materials that are suitable as a FPC may have a KI, as defined above, from about 800 to about 1500, alternatively about 900 to about 1200, alternatively about 1000 to about 1100, alternatively about 1000.

Exemplary perfume compositions are disclosed, for example, in U.S. patent application Ser. No. 14/024,673, titled "INK JET DELIVERY SYSTEM COMPRISING AN IMPROVED PERFUME MIXTURE".

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of connecting a microfluidic delivery refill with a housing, wherein the microfluidic delivery refill comprises a rigid microfluidic delivery member having a die and electrical leads that are in electrical communication with the die, wherein the electrical leads terminate at electrical contacts, wherein the electrical contacts are disposed on a first plane, wherein the microfluidic delivery refill comprises a reservoir that contains a perfume composition, wherein the die comprises a silicon support substrate and a conductive layer that is disposed on the silicon support substrate, wherein the conductive layer comprises at least one heater, wherein the housing comprises electrical contacts, the method comprising the steps of:
   electrically connecting the electrical contacts of the microfluidic delivery refill with the electrical contacts of the housing by sliding the microfluidic delivery refill toward an interior of the housing in only one direction that is parallel with the first plane.

2. The method according to claim 1, wherein the housing comprises a fan.

3. The method according to claim 1, wherein the microfluidic delivery refill includes a piezoelectric material or a heater.

4. The method according to claim 1, wherein the microfluidic delivery system is powered by battery.

5. The method according to claim 1, wherein the transfer member is configured to wick the fluid composition upward from the reservoir and toward the microfluidic delivery member, in opposition to the force of gravity.

6. The method according to claim 1, wherein the microfluidic delivery system comprises at least one sensor.

7. The method according to claim 1, wherein the microfluidic delivery system is powered by an AC outlet.

8. The method according to claim 1 further comprising the step of removing the microfluidic delivery refill from the housing by moving the microfluidic delivery refill in a direction parallel with the first plane.

\* \* \* \* \*